(12) United States Patent
Johannaber et al.

(10) Patent No.: US 10,842,636 B2
(45) Date of Patent: Nov. 24, 2020

(54) DEVICE FOR SENSING IMPLANT LOCATION AND IMPINGEMENT

(71) Applicant: Zimmer, Inc., Warsaw, IN (US)

(72) Inventors: Kenneth D. Johannaber, Reno, NV (US); John Minck, Jr., Reno, NV (US); Rida Hariri, Reno, NV (US); Derek Dalbey, Reno, NV (US)

(73) Assignee: Zimmer, Inc., Warsaw, IN (US)

( * ) Notice: Subject to any disclaimer, the term of this patent is extended or adjusted under 35 U.S.C. 154(b) by 18 days.

(21) Appl. No.: 15/800,915

(22) Filed: Nov. 1, 2017

(65) Prior Publication Data

US 2018/0116805 A1     May 3, 2018

Related U.S. Application Data

(60) Provisional application No. 62/416,435, filed on Nov. 2, 2016, provisional application No. 62/514,257, filed on Jun. 2, 2017.

(51) Int. Cl.
*A61F 2/34* (2006.01)
*A61F 2/32* (2006.01)
(Continued)

(52) U.S. Cl.
CPC .............. *A61F 2/34* (2013.01); *A61B 5/0031* (2013.01); *A61B 5/05* (2013.01); *A61B 5/4571* (2013.01); *A61B 5/4851* (2013.01); *A61B 5/7445* (2013.01); *A61F 2/32* (2013.01); *A61F 2/3609* (2013.01); *A61F 2/4657* (2013.01); *A61F 2/4684* (2013.01); *A61B 2018/00773* (2013.01); *A61F 2002/2828* (2013.01);
(Continued)

(58) Field of Classification Search
USPC ...................................... 623/18.12
See application file for complete search history.

(56) References Cited

U.S. PATENT DOCUMENTS

| 5,108,400 A | 4/1992 | Appel et al. |
| 7,300,432 B2 | 11/2007 | Surma et al. |

(Continued)

FOREIGN PATENT DOCUMENTS

| CN | 103735303 | 4/2014 |
| CN | 110035716 A | 7/2019 |

(Continued)

OTHER PUBLICATIONS

"International Application Serial No. PCT/US2017/059552, International Search Report dated Feb. 20, 2018", 4 pgs.

(Continued)

*Primary Examiner* — David H Willse
*Assistant Examiner* — Javier G Blanco
(74) *Attorney, Agent, or Firm* — Schwegman Lundberg & Woessner, P.A.

(57) ABSTRACT

Embodiments of a system and method for assessing hip arthroplasty component movement are generally described herein. A method may include receiving data from a sensor embedded in a femoral head component, the femoral head component configured to fit in an acetabular component, determining information about a magnetic field from the data, and outputting an indication of an orientation, coverage, or a force of the femoral head component relative to the acetabular component.

16 Claims, 19 Drawing Sheets

(51) Int. Cl.
*A61F 2/46* (2006.01)
*A61B 5/00* (2006.01)
*A61B 5/05* (2006.01)
*A61F 2/36* (2006.01)
*A61F 2/30* (2006.01)
*A61F 2/48* (2006.01)
*A61B 18/00* (2006.01)
*A61F 2/28* (2006.01)

(52) U.S. Cl.
CPC ............... *A61F 2002/3055* (2013.01); *A61F 2002/3067* (2013.01); *A61F 2002/30079* (2013.01); *A61F 2002/3611* (2013.01); *A61F 2002/3625* (2013.01); *A61F 2002/4658* (2013.01); *A61F 2002/4666* (2013.01); *A61F 2002/4668* (2013.01); *A61F 2002/4696* (2013.01); *A61F 2002/4698* (2013.01); *A61F 2002/482* (2013.01)

(56) References Cited

U.S. PATENT DOCUMENTS

| | | | |
|---|---|---|---|
| 8,167,823 B2 | 5/2012 | Nycz et al. | |
| 8,393,409 B2 | 3/2013 | Pedicini | |
| 8,695,726 B2 | 4/2014 | Pedicini | |
| 9,414,940 B2 | 8/2016 | Stein et al. | |
| 10,660,760 B2 | 5/2020 | Johannaber et al. | |
| 10,792,162 B2 | 10/2020 | Johannaber et al. | |
| 2002/0101232 A1 | 8/2002 | Mendes et al. | |
| 2004/0243148 A1* | 12/2004 | Wasielewski | A61B 17/00 606/130 |
| 2005/0010301 A1* | 1/2005 | Disilvestro | A61B 5/076 623/18.12 |
| 2005/0101962 A1 | 5/2005 | Schwenke et al. | |
| 2006/0069447 A1 | 3/2006 | Disilvestro et al. | |
| 2006/0271199 A1 | 11/2006 | Johnson | |
| 2007/0005145 A1 | 1/2007 | Banks et al. | |
| 2007/0149981 A1 | 6/2007 | Bhattacharyya | |
| 2008/0065225 A1* | 3/2008 | Wasielewski | A61B 5/03 623/18.11 |
| 2008/0294258 A1 | 11/2008 | Revie et al. | |
| 2010/0217156 A1 | 8/2010 | Fisher et al. | |
| 2010/0331734 A1 | 12/2010 | Stein | |
| 2010/0331737 A1 | 12/2010 | Stein et al. | |
| 2010/0332152 A1 | 12/2010 | Stein | |
| 2011/0093087 A1* | 4/2011 | Mcmahon | A61F 2/34 623/22.42 |
| 2011/0319755 A1* | 12/2011 | Stein | A61B 5/0031 600/437 |
| 2012/0220430 A1 | 8/2012 | Bucar et al. | |
| 2013/0090737 A1 | 4/2013 | Flaherty et al. | |
| 2013/0197656 A1 | 8/2013 | Conrad | |
| 2014/0249535 A1* | 9/2014 | McCarthy | A61F 2/4684 606/91 |
| 2014/0330281 A1 | 11/2014 | Aghazadeh | |
| 2015/0018718 A1 | 1/2015 | Aghazadeh | |
| 2015/0196343 A1 | 7/2015 | Donald et al. | |
| 2015/0282856 A1 | 10/2015 | Haiat et al. | |
| 2015/0289890 A1* | 10/2015 | Chen | A61F 2/4657 606/102 |
| 2015/0297362 A1 | 10/2015 | Singh et al. | |
| 2016/0029952 A1 | 2/2016 | Hunter et al. | |
| 2017/0007330 A1 | 1/2017 | Britton et al. | |
| 2018/0161168 A1 | 6/2018 | Johannaber et al. | |
| 2020/0276023 A1 | 9/2020 | Johannaber et al. | |

FOREIGN PATENT DOCUMENTS

| | | |
|---|---|---|
| CN | 110049748 A | 7/2019 |
| DE | 10342823 | 4/2005 |
| DE | 102008005180 | 11/2008 |
| EP | 2335651 | 6/2011 |
| EP | 3058865 | 8/2016 |
| WO | 2013117909 | 8/2013 |
| WO | WO-2014144107 A1 * | 9/2014 ........... A61F 2/4657 |
| WO | WO-2018111429 A1 | 6/2018 |

OTHER PUBLICATIONS

"International Application Serial No. PCT/US2017/059552, Written Opinion dated Feb. 20, 2018", 7 pgs.

"International Application Serial No. PCT US2017 059565, International Search Report dated Feb. 26, 2018", 5 pgs.

"International Application Serial No. PCT US2017 059565, Written Opinion dated Feb. 26, 2018", 8 pgs.

"International Application Serial No. PCT US2017 059559, International Search Report dated Mar. 5, 2018", 5 pgs.

"International Application Serial No. PCT US2017 059559, Written Opinion dated Mar. 5, 2018", 9 pgs.

U.S. Appl. No. 15/800,932, filed Nov. 1, 2017, Device for Sensing Implant Location and Impingement.

U.S. Appl. No. 15/800,988, filed Nov. 1, 2017, Impact Force Feedback Display System.

U.S. Appl. No. 15/801,025, filed Nov. 1, 2017, Shoulder Arthroplasty Trial Sensors.

"U.S. Appl. No. 15/801,025, Response filed Jun. 27, 2019 to Restriction Requirement dated May 1, 2019", 7 pgs.

"U.S. Appl. No. 15/801,025, Restriction Requirement dated May 1, 2019", 6 pgs.

"U.S. Appl. No. 15/800,932, Non Final Office Action dated Oct. 31, 2019", 20 pgs.

"U.S. Appl. No. 15/800,932, Response filed Oct. 8, 2019 to Restriction Requirement dated Aug. 8, 2019", 8 pgs.

"U.S. Appl. No. 15/800,932, Restriction Requirement dated Aug. 8, 2019", 8 pgs.

"U.S. Appl. No. 15/800,988, Response filed Nov. 11, 2019 to Restriction Requirement dated Oct. 8, 2019", 7 pgs.

"U.S. Appl. No. 15/800,988, Restriction Requirement dated Oct. 8, 2019", 7 pgs.

"U.S. Appl. No. 15/801,025, Non Final Office Action dated Aug. 22, 2019", 14 pgs.

"Australia Application Serial No. 2017354043, First Examination Report dated Jun. 27, 2019", 3 pgs.

"Australia Application Serial No. 2017354043, Response filed Jul. 23, 2019 First Examination Report dated Jun. 27, 2019", 8 pgs.

"U.S. Appl. No. 15/801,025, Response Filed Nov. 21, 2019 to Non-Final Office Action dated Aug. 22, 2019", 13 pages.

"U.S. Appl. No. 15/800,932, Notice of Allowance dated Mar. 18, 2020", 11 pgs.

"U.S. Appl. No. 15/800,932, Response filed Jan. 31, 2020 to Non Final Office Action dated Oct. 31, 2019", 12 pgs.

"U.S. Appl. No. 15/800,988, Non Final Office Action dated Feb. 20, 2020", 11 pgs.

"U.S. Appl. No. 15/801,025, Response Filed Mar. 23, 2020 to Notice of Non-Responsive Amendment", 10 pgs.

"Australian Application Serial No. 2019264529, First Examination Report dated Mar. 17, 2020", 4 pgs.

"Canadian Application Serial No. 3,042,672, Response filed Mar. 20, 2020 to Office Action dated Nov. 21, 2019", 11 pgs.

"European Application Serial No. 17804724.7, Response to Communication pursuant to Rules 161(1) and 162 EPC filed Feb. 3, 2020", 10 pgs.

"European Application Serial No. 17817317.5, Response to Communication pursuant to Rules 161(1) and 162 EPC filed Jan. 2, 2020", 88 pages.

"Canadian Application Serial No. 3,042,672, Office Action dated Nov. 21, 2019", 3 pages.

"U.S. Appl. No. 15/800,988, Response filed May 20, 2020 to Non Final Office Action dated Feb. 20, 2020", 9 pages.

"U.S. Appl. No. 16/875,408, Preliminary Amendment filed Jun. 10, 2020", 7 pages.

"U.S. Appl. No. 15/801,025, Notice of Allowance dated Jun. 2, 2020", 10 pages.

"U.S. Appl. No. 15/800,988, Final Office Action dated Jun. 5, 2020", 13 pages.

(56) References Cited

OTHER PUBLICATIONS

"Australian Application Serial No. 2019264529, Response filed Jul. 30, 2020 to Subsequent Examiners Report dated Jul. 27, 2020", 12 pages.
"Canadian Application Serial No. 3,045,624, Office Action dated May 12, 2020", 5 pages.
"Australian Application Serial No. 2019264529, Subsequent Examiners Report dated Jul. 27, 2020", 2 pages.
"Australian Application Serial No. 2019264529, Response filed Jun. 30, 2020 to First Examination Report dated Mar. 17, 2020", 19 pages.
"Chinese Application Serial No. 201780072439.7, Office Action dated Aug. 19, 2020", with English translation, 21 pages.
"Canadian Application Serial No. 3,045,624, Response filed Sep. 10, 2020 to Office Action dated May 12, 2020", 13 pages.
U.S. Appl. No. 17/001,235, filed Aug. 24, 2020, Shoulder Arthroplasty Trial Sensors.
"U.S. Appl. No. 15/801,025, Corrected Notice of Allowability dated Aug. 13, 2020", 2 pages.
"U.S. Appl. No. 15/800,988, Response filed Sep. 8, 2020 to Final Office Action dated Jun. 5, 2020", 9 pages.
"U.S. Appl. No. 15/800,988, Advisory Action dated Sep. 15, 2020", 3 pages.

\* cited by examiner

US 10,842,636 B2

DEVICE FOR SENSING IMPLANT LOCATION AND IMPINGEMENT

CLAIM OF PRIORITY

This application claims the benefit of U.S. Provisional Patent Application Ser. No. 62/416,435, filed on Nov. 2, 2016, and also claims the benefit of U.S. Provisional Patent Application Ser. No. 62/514,257, filed on Jun. 2, 2017, the benefit of priority of each of which is claimed hereby, and each of which are incorporated by reference herein in its entirety.

BACKGROUND

Dislocation, leg length discrepancy, and general instability are the leading complications with total hip arthroplasty. These problems are difficult to anticipate and often are not detectable using traditional methods during or immediately after surgery. Some methods to attempt to detect these issues include running a finger along an acetabular cup during range of motion trials to detect impingement. Other methods for cup alignment target a standard inclination or anteversion angle, which may not be appropriate for all patients. Additionally, other methods for determining coverage are often inaccurate. Surgeons typically use tactile feedback such as palpating, articulating with a finger behind the joint, to assess coverage subjectively.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
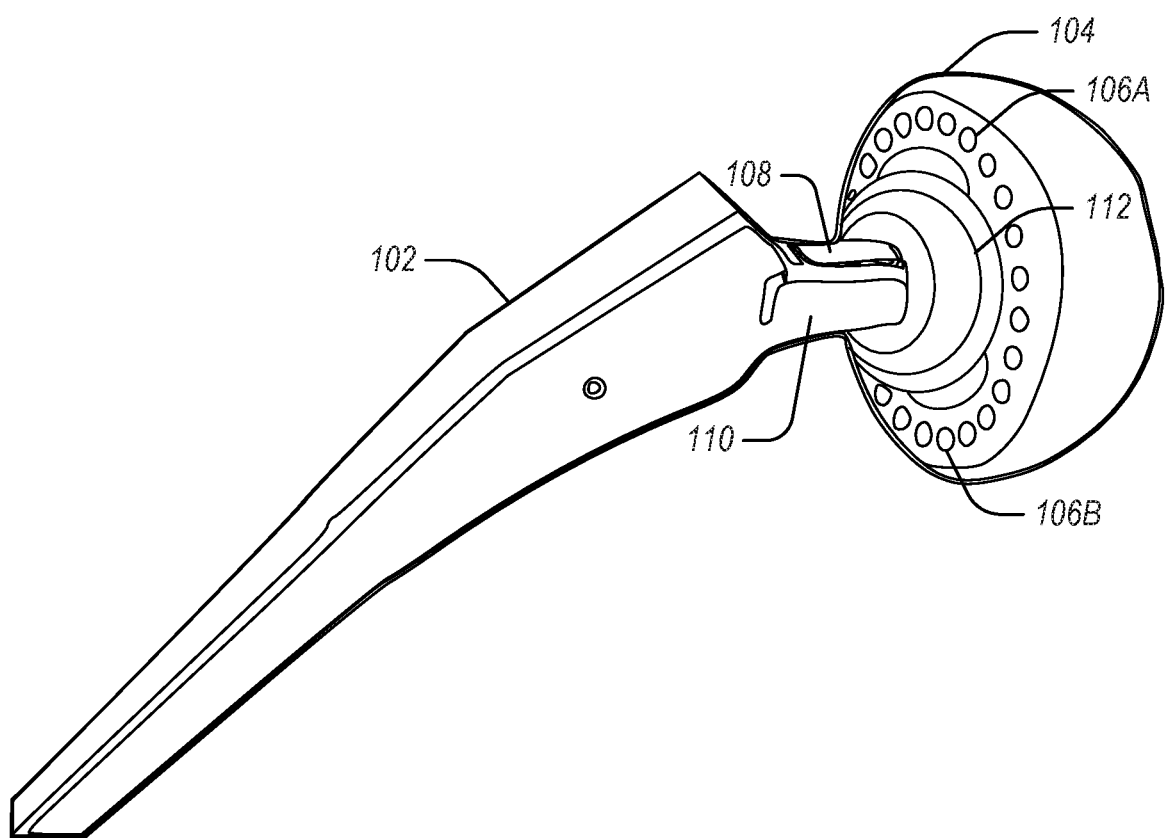
FIG. 1 illustrates a hip arthroplasty system with a sensor in a trunnion in accordance with some embodiments.

Systems and methods for assessing hip arthroplasty component movement are described herein. The systems and methods herein assess joint stability, range of motion, and risk of impingement to help prevent postoperative impingement or dislocation, such as in cases of total hip arthroplasty. The systems and methods described herein may provide a risk of impingement intraoperatively. Data received from the systems and methods described herein may be used to determine how impingement position affects outcomes and also used to modify assessment and surgical techniques to improve outcomes. In an example, the systems and methods described herein may be used with a ball and socket joint (e.g., in a shoulder surgical procedure).

Total hip arthroplasty includes a femoral implant and an acetabular component, such as a cup or liner that interact at a joint. The femoral implant includes a femoral head to fit into the acetabular component. In an example, the systems and methods described herein provide a quantified value of a proximity of the neck or trunnion of the femoral implant to the acetabular component. While the systems and methods herein describe implant-to-implant impingement, they may also be used to describe implant-to-bone and bone-to-bone impingement.

The surgeon may use an output of the disclosed systems and methods intraoperatively while putting a joint through a range of motion test to capture a fit of the acetabular component to the femoral head at different points in the range of motion. The output may include a risk-level for postoperative impingement. The output may include an indicator of a patient-specific assessment of acetabular component to femoral head. In an example, the output may include an indicator of impingement, as well as an indicator of risk of impingement through proximity sensing. The systems and methods described herein may be used around the perimeter of the acetabular component, including at points that may not be accessible to a surgeon visibly or with a finger, such as during a range of motion test.

In an example, data may be collected from a system intraoperatively and postoperatively to determine a level of success for preventing impingement, dislocation, or other complications. The data may be used in a feedback system applying techniques (e.g., adaptive or customized approaches, such as those which may involve machine learning) to improve precision of the system or outcomes for a patient. In an example, a sensor may be used to collect data that may be used to establish patient-specific surgical techniques or postoperative care. Data output may include proximity to impingement at certain points in a range of motion trial. If risk of impingement is high, postoperative guidance may include longer recovery with limited activity requirements. The machine learning techniques may be used to establish a standard or customized acetabular component position algorithm.

In an example, a surgeon may use an output of the systems and methods described herein while performing range of motion tests with a joint to capture an orientation and extent of coverage between the femoral head and the acetabular component, such as at different points in the range of motion. The output may be used to map the coverage to the range of motion position, which may indicate risk factors for dislocation. The output may be used to assess laxity during a shuck test (e.g., distraction of the joint), or the output may be used to define precursors for impingement.

FIG. 1 illustrates a hip arthroplasty system 100 with a sensor 108 in a trunnion 110 in accordance with some embodiments. The hip arthroplasty system 100 includes a femoral implant 102 (which may be a femoral trial), with a femoral head 112 at a distal end of the femoral implant. The femoral implant includes the trunnion 110 with the sensor 108. The femoral head 112 is configured to fit in an acetabular component 104. The acetabular component 104 includes a plurality of magnets (e.g., 106A and 106B) or a magnet ring. The plurality of magnets (e.g., 106A and 106B) or the magnet ring may be removable from the acetabular component 104. The acetabular component 104 may be a cup or a liner. In an example, one or more of the acetabular component 104, the femoral head 112, the trunnion 110, or other components described herein may be implant components, trial components, testing components, or the like.

The hip arthroplasty system 100 may be used to indicate a possibility of impending impingement between the implant neck (e.g., the trunnion 110) and the acetabular component 104. The sensor 108 may include a Hall effect sensor, a reed switch, a magnetometer or another type of proximity sensor, to detect a distance between the trunnion 110 and the acetabular component 104 (e.g., the plurality of magnets 106A, 106B, etc.). The plurality of magnets (e.g., 106A, 106B, etc.) or a magnet ring on the acetabular component 104 may supplies a reference magnetic field, to be measured or detected by the sensor 108. In an example, the plurality of magnets (e.g., 106A or 106B) may be embedded in a ring and attached to the acetabular component 104, such as with surgical glue, tension, screws, or other attachment means. In another example, the ring may have a continuous sheet magnet.

In an example, a plurality of sensors may be used to collect data. The sensor 108 may be embedded into the trunnion 110, which may be disposable or reusable. In an example, the trunnion 110 may include a printed circuit board for receiving the sensor data, forwarding the sensor data, or processing the sensor data.

The sensor 108 may be positioned at a perimeter of the trunnion 110. The sensor 108 may output a voltage in response to magnetic field strength, such as a field emanating from one or more of the plurality of magnets (e.g., 106A or 106B). As the trunnion 110 is rotated toward the magnetic ring, the voltage output may increase, indicating the closer distance. The hip arthroplasty system 100 may be calibrated to output a voltage as a distance offset (such as in millimeters, inches, or degrees, etc.) to output an indicator of how close the trunnion 110 is to the acetabular component 104 or whether there is a risk of impingement. The output may be consistent for the entire circumference of the acetabular component 104. For example, an assessment may be made as to whether an adjustment is needed in the acetabular component 104 position relative to a high-risk area, such as during a range of motion assessment.

Figure 2A:
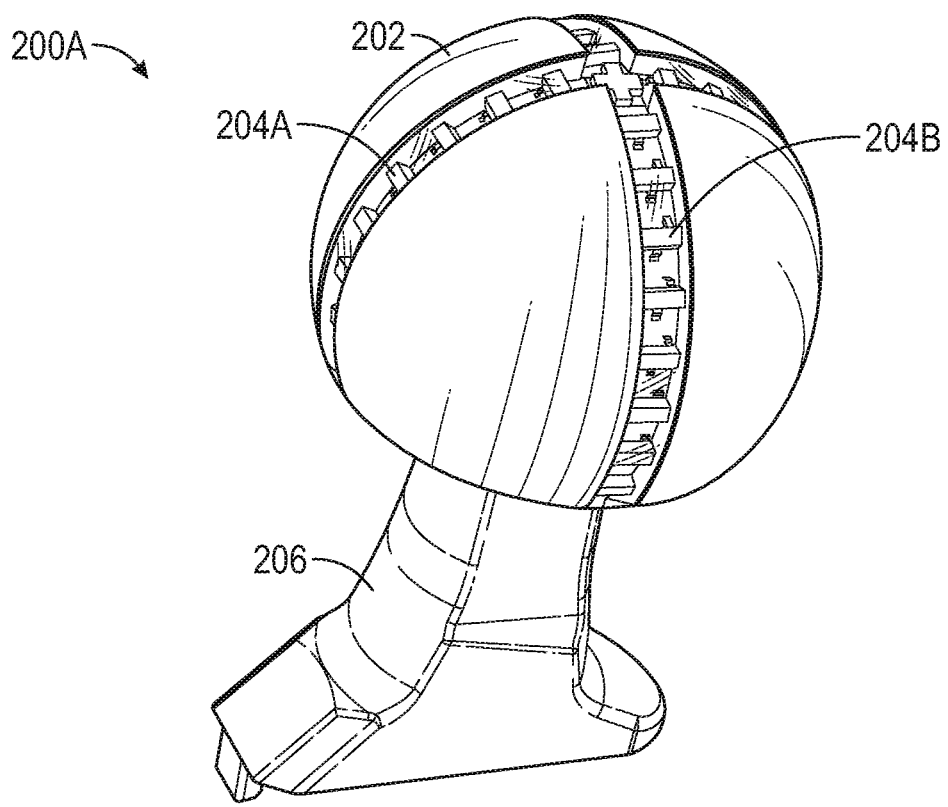
FIGS. 2A-2C illustrate a hip arthroplasty system with sensors arranged in two intersecting arcs within a femoral head in accordance with some embodiments.
Figure 2B:
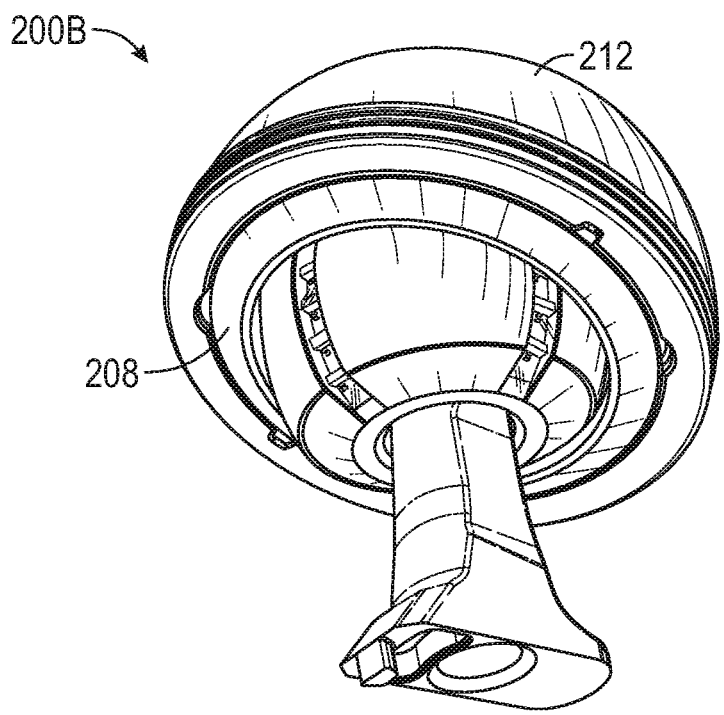
Figure 2C:
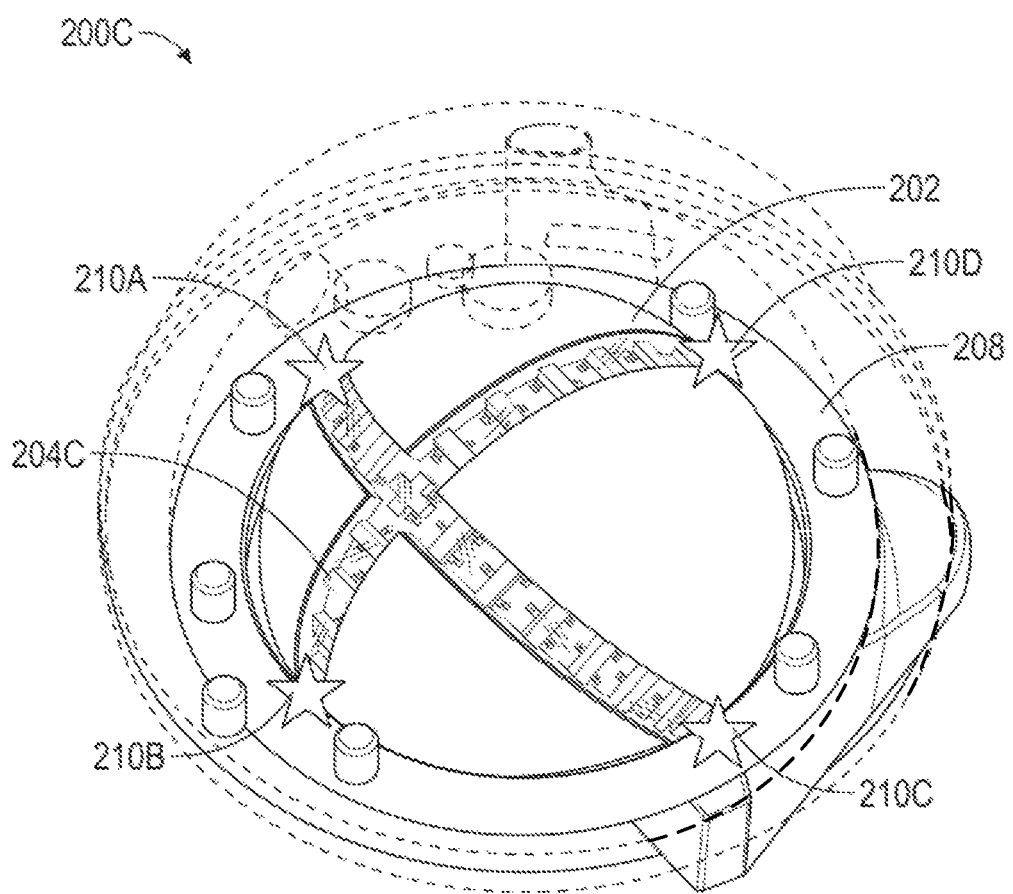

FIGS. 2A-2C illustrate a hip arthroplasty system 200A-200C with sensors (e.g., sensor 204A, 204B, 204C, etc.) arranged in two intersecting arcs within a femoral head 202 in accordance with some embodiments. The femoral head 202 may be connected to a trunnion 206 of a femoral implant. The femoral head 202 may be configured to fit into an acetabular component 212. The acetabular component 212 may include a magnetic ring 208 or a plurality of magnets. The magnetic ring 208 or the plurality of magnets may be removable or embedded in the acetabular component 212.

In FIG. 2C, the hip arthroplasty system 200C is shown with the acetabular component 212 hidden to illustrate the interaction of the magnetic ring 208 with the plurality of sensors (e.g., 204C) at interaction points 210A-210D. From the interaction points 210A-210D, the hip arthroplasty system 200C may be used to determine an angle of impingement of the acetabular component 212 (using the magnetic ring 208) to the trunnion 206.

In an example, the femoral head 202 includes two circumferential rings of Hall effect sensors (e.g., 204A, 204B, 204C), the sensors to output a proximity to a magnetic field. The magnetic field may be supplied by the magnetic ring 208, which may be removable from the acetabular component or may be embedded in the acetabular component. In an example, the Hall effect sensors may experience a spike (e.g., output an increased voltage from a first state) when near the magnetic field. The interaction points 210A-210D may correspond with four different sensors in the femoral head 202, each of which may experience a spike or output a higher voltage than the remaining sensors. The voltage output may be directly proportional to the strength of the magnetic field. As a result, the sensor closest to the magnetic ring may return the largest voltage spike. The interaction points 210A-210D represent points where the Hall effect sensors cross the magnetic ring 208. These four interaction points 210A-210D may be used to create a plane, which may be used to provide a coverage map of the femoral head 202 in the acetabular component.

In an example, the femoral head 202 may include two perpendicular rows of position sensors (e.g., Hall effect sensors or magnetometers) that interact (e.g., magnetically) with the magnetic ring 208 attached to the acetabular component (e.g., a liner, cup, or shell). The output from the sensors may be sent to a system to interprets the output and perform a data analysis. The data analysis may be used to determine whether an impingement has occurred or is likely to occur postoperatively. By placing two perpendicular arcs of sensors along the femoral head 202 from an edge to an opposite edge along a half-circumference, and placing the magnetic ring 208 on the perimeter of the opening of the acetabular component, the hip arthroplasty system 200A-200C facilitates the output of the four interaction points 210A-210D, which correspond to the sensors that are closest to the magnet. Since the location of each sensor on the femoral head 202 is known, the interaction points 210A-210D may be converted into a plane that can be interpreted as coverage between the femoral head 202 and the acetabular component. The plane may be tracked, such as in real-time, for example as the joint runs through range of motion trials.

In an example, the hip arthroplasty system 200A-200C may be used to identify issues intraoperatively. For example, separation of the femoral head 202 and the acetabular component may be identified via translation, such as when the interaction points 210A-210D translate instead of rotate. This is described in further detail below in FIGS. 3A-3B.

Figure 4A:
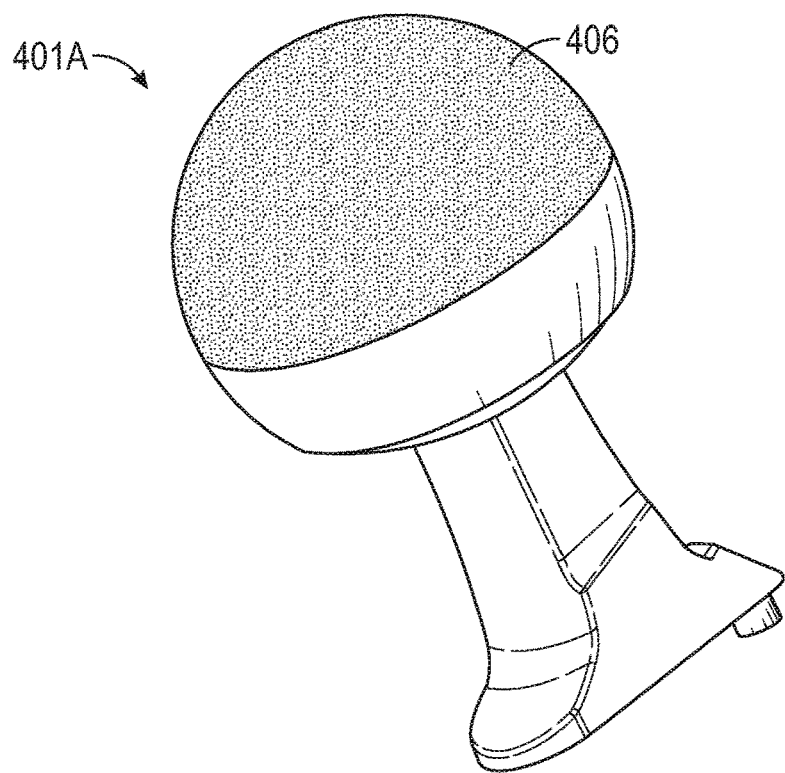
FIGS. 4A-4D illustrate visual indications of a degree of impingement of an acetabular component to a femoral head in accordance with some embodiments.
Figure 4B:
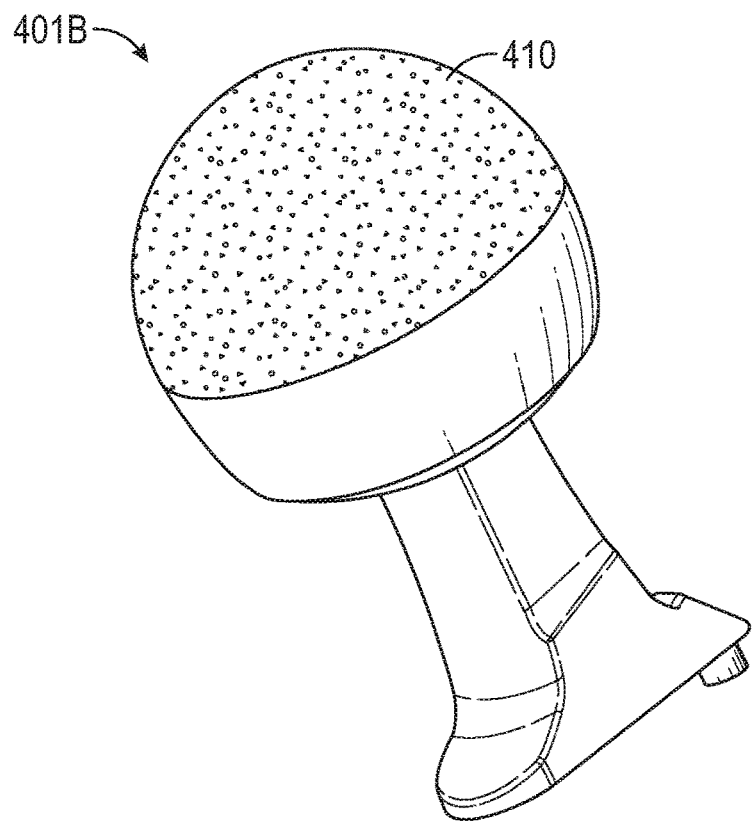

In another example, impingement or impingement risk may be identified, such as when an interaction point e.g., 210A is high and an opposite interaction point, e.g., 210C is low on the femoral head 202. This is described in further detail below in FIGS. 4A-4B.

Figure 3A:
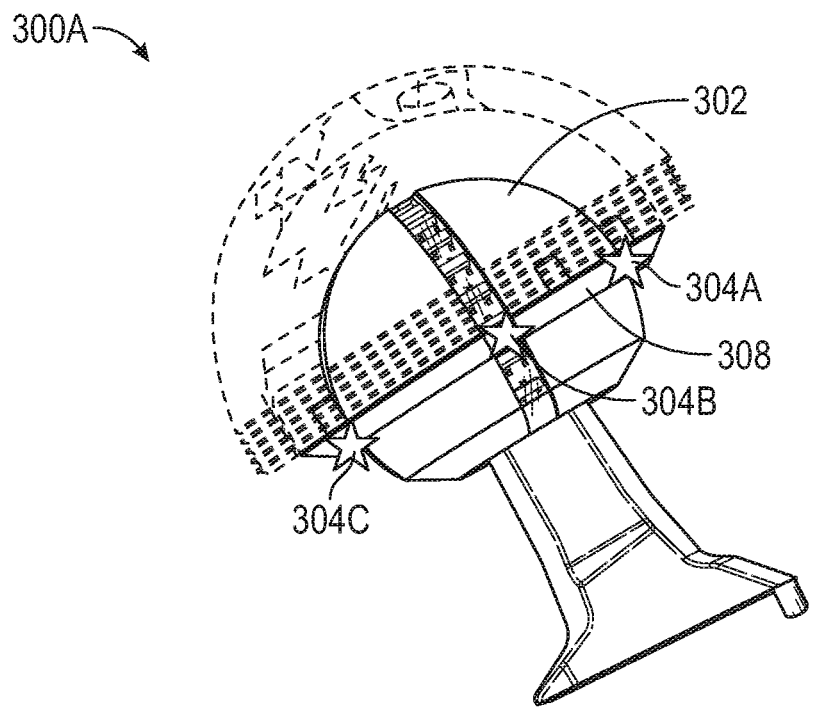
FIGS. 3A-3D illustrate femoral implants including representations of a degree of separation of an acetabular component to a femoral head in accordance with some embodiments.

FIGS. 3A-3D illustrate femoral implants (e.g., 300A-300D) or trials including representations of a degree of separation of an acetabular component (hidden for clarity) to a femoral head 302 in accordance with some embodiments. The femoral implant 300A illustrates an interaction between the femoral head 302 and a magnetic ring 308 (representative of the acetabular component). The interaction includes a plurality of interaction points (e.g., 304A-304C). In FIG. 3A, the interaction points (e.g., 304A-304C) may be used to determine that the femoral head 302 is fully inserted into the acetabular component (as represented by the magnetic ring 308). For example, the interaction points 304A-304C are at a level of a third sensor from bottom (e.g., closest to the trunnion of the femoral head 302) at three sides of the femoral head 302. The location of the interaction points 304A-304C indicate that the femoral head 302 is fully inserted in the acetabular component and in a non-flexed and non-rotated position.

Figure 3B:
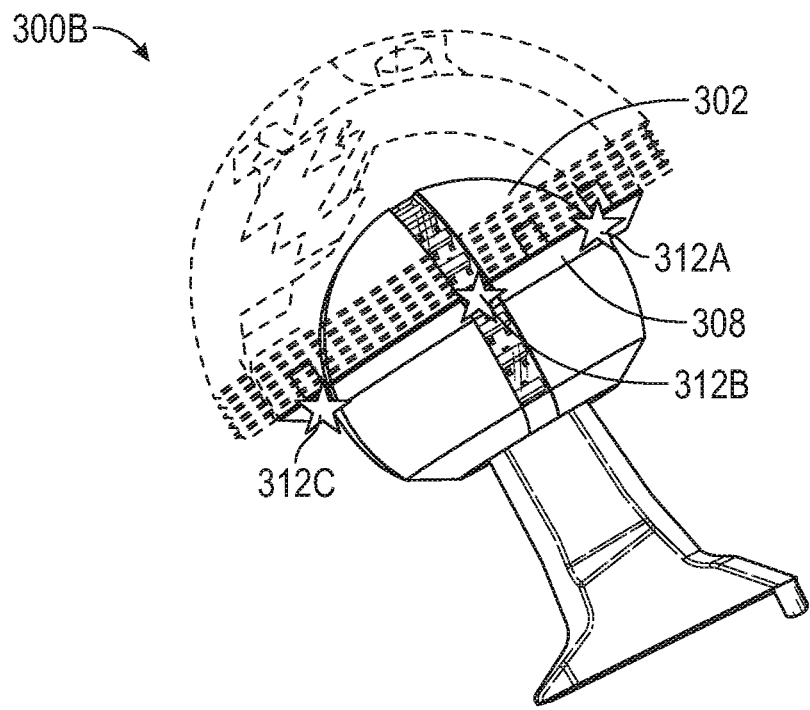

The femoral implant 300B illustrates an interaction between the femoral head 302 and a magnetic ring 308 (representative of the acetabular component). The interaction includes a plurality of interaction points (e.g., 312A-312C). In contrast to FIG. 3A, FIG. 3B shows the interaction points (e.g., 312A-312C) at a different altitude of insertion. The interaction points (e.g., 312A-312C) detected in the real representation 300B may be used to determine that the femoral head 302 is not fully inserted into the acetabular component (as represented by the magnetic ring 308). For example, the interaction points 312A-312C are at a level of a fourth sensor from bottom (e.g., closest to the trunnion of the femoral head 302) at three sides of the femoral head 302. The location of the interaction points 312A-312C indicate that the femoral head 302 is not fully inserted in the acetabular component and that separation has occurred.

The femoral implant 300C shows the femoral head 302 fitting in the acetabular component. The femoral head 302 includes a plurality of sensors that interact with the magnetic ring 308 at interaction points (e.g., 314A-314C). The interaction points (e.g., 314A-314C) may be used to determine an angle of fit for the acetabular component with the femoral head 302.

Figure 3C:
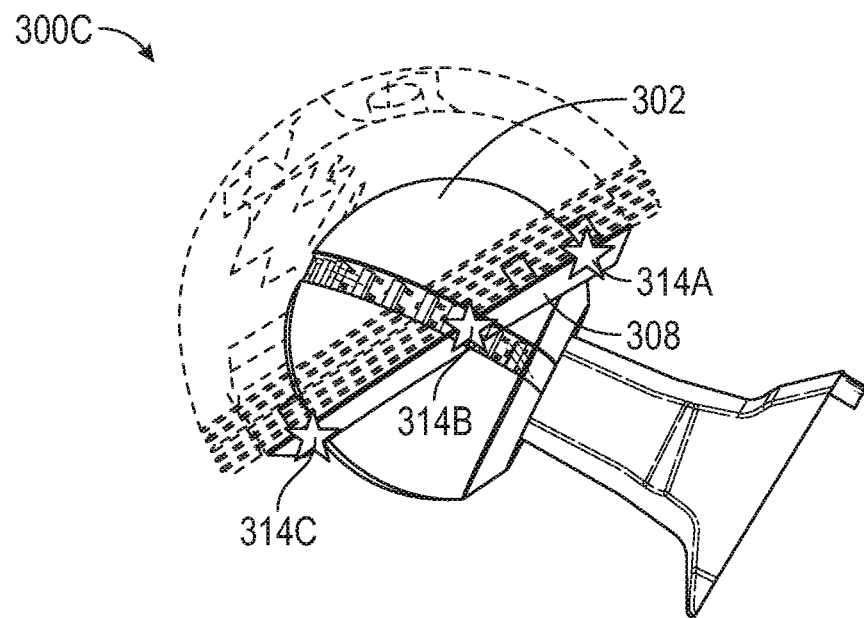
Figure 3D:
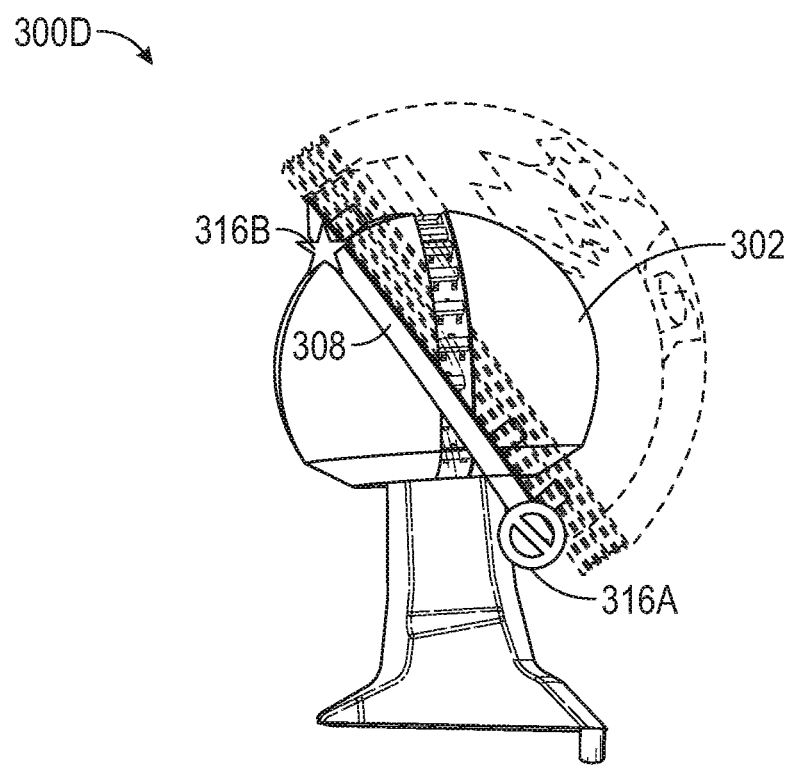

For example, the interaction points 314A-314C are located at positions coincident with sensors at the three sides visible in FIG. 3C of the femoral head 302. Further, the location of interaction point 314C is at a sensor below an upper limit sensor, such that interaction point 314A is also at a sensor. The location of the interaction points 314A-314C indicate that the femoral head 302 is rotating properly within the acetabular component. When the rotation that is shown in the femoral implant 300C is at an extreme range of motion (e.g., a leg is fully flexed, fully straightened, etc.), then over rotation and impingement are unlikely to have occurred or may be unlikely to occur.

The femoral implant 300D shows the femoral head 302 fitting in the acetabular component. The femoral head 302 includes a plurality of sensors that interact with the magnetic ring 308 at interaction points (e.g., 316A-316B). The interaction points (e.g., 316A-316B) may be used to determine an angle of fit for the acetabular component with the femoral head 302. In the femoral implant 300D, the fit is shown within a predefined limit at the interaction point 316B and outside a predefined limit at the interaction point 316A.

For example, the location of interaction point 316B is at a sensor above the upper limit sensor, such that interaction point 316A is not at a sensor. The location of the interaction points 316A-316B may indicate that the femoral head 302 is over rotated within the acetabular component. The rotation that is shown in the femoral implant 300D indicates that over rotation may have occurred and impingement is possible or may occur in the future.

FIGS. 4A-4D illustrate visual indications (e.g., 401A-401D) of a degree of impingement of an acetabular component (hidden for clarity) to a femoral head in accordance with some embodiments. For example, the full insertion shown in FIG. 3A is represented by a positive indication 406 in the virtual representation 401A. The partial insertion shown in FIG. 3B is represented by a negative indication 410 in the virtual representation 401B. The virtual representation 401C indicates rotation and provides a real-time assessment of the mating surface between a femoral head and an acetabular component (e.g., low risk of impingement), such as those shown in FIG. 3C.

Figure 4C:
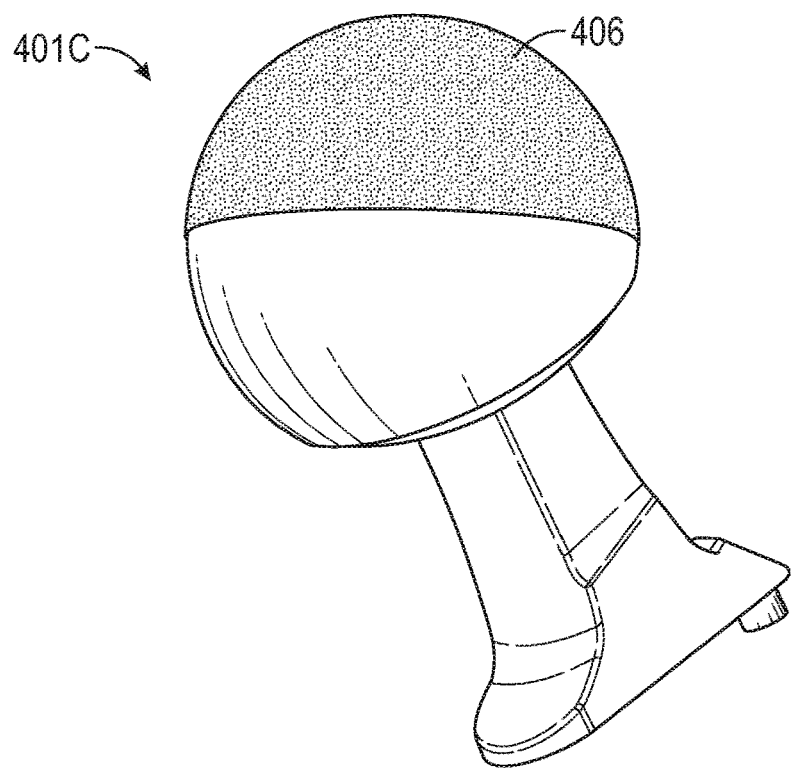
Figure 4D:
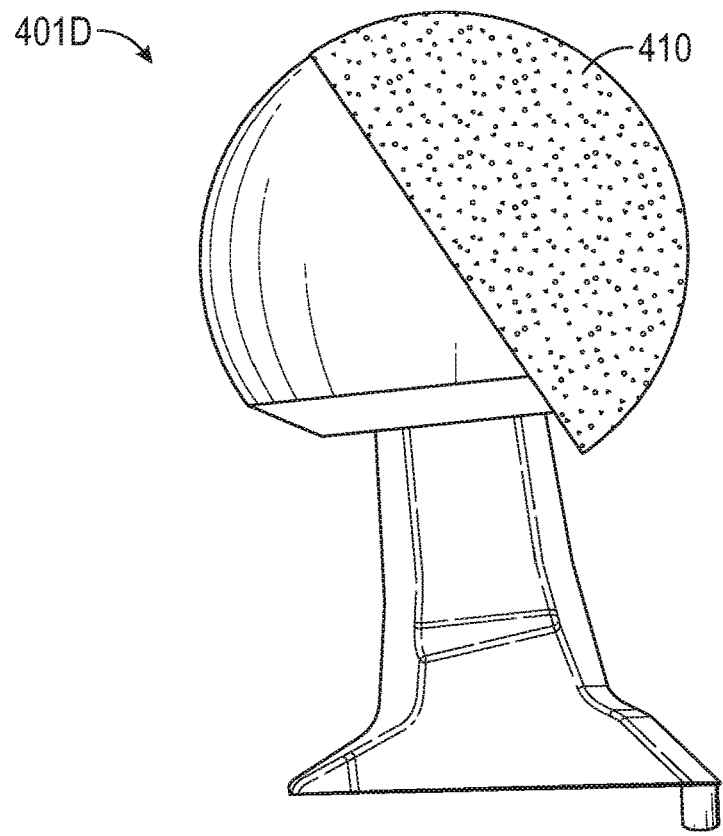

In the femoral implant 300C of FIG. 3C, the fit is shown within predefined limits, and the visual indication 401C of FIG. 4C illustrates the positive indication 406. In representing the femoral implant 300D of FIG. 3D, the visual indication 401D illustrates the negative indication 410 to show that there is a potential problem with the acetabular component or the femoral head based on the interaction point 412A of FIG. 3D. The virtual representation 401D of FIG. 4D indicates that rotation has occurred and provides a real-time assessment of the mating surface between the femoral head and the acetabular component (e.g., high risk of impingement), such as those shown in FIG. 3D.

Figure 5:
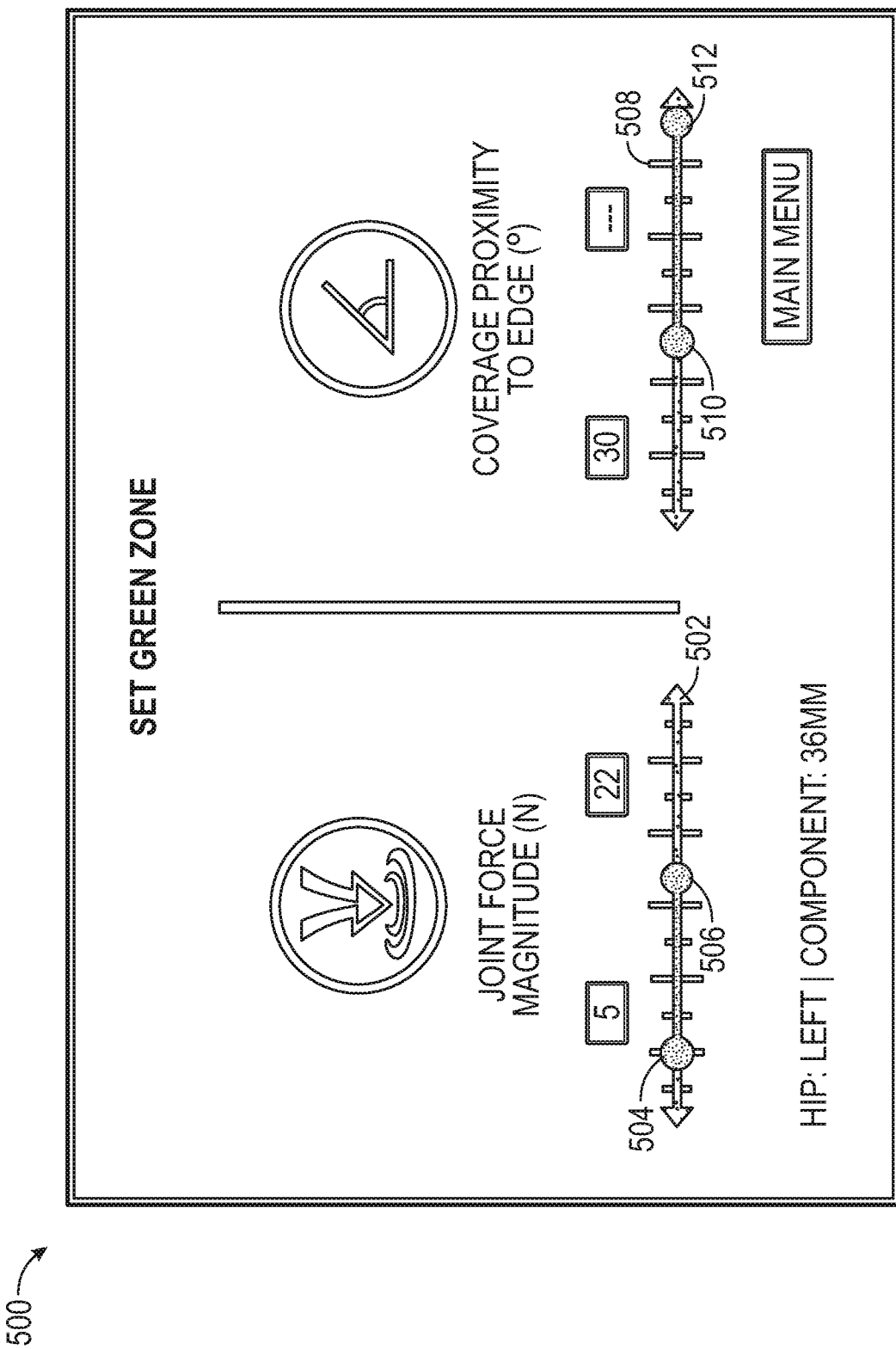
FIG. 5 illustrates a user interface for setting joint force and proximity angle limits in accordance with some embodiments.

FIG. 5 illustrates a user interface 500 for setting joint force and proximity angle limits in accordance with some embodiments. The user interface 500 includes a joint force magnitude scale 502 and a coverage proximity to edge scale 508. The joint force magnitude scale 502 includes a lower slider 504 and an upper slider 506 for selecting a joint force magnitude minimum and maximum, respectively. The coverage proximity to edge scale 508 includes a lower slider 510 and an upper slider 512 for selecting a coverage proximity angle minimum and maximum, respectively.

The user interface 500 allows a user to set the joint force magnitude limits (low and high) and the low limit of the angle between the liner rim and the central force axis (e.g., 'coverage'). In an example, the user interface 500 may allow the user to input basic information about the case or pre-operative planning requirements. This input may be used, along with the limits and the data received from sensors intraoperatively to create a personalized postoperative care plan. The data and input may be used in a feedback process, along with postoperative outcomes, to improve the functioning of intraoperative assessments of femoral head and acetabular component fit. In another example, limits may be recommended to the user on the user interface 500, such as machine learned limits from past data, which may, for example, take into account individual patient information.

Figure 6A:
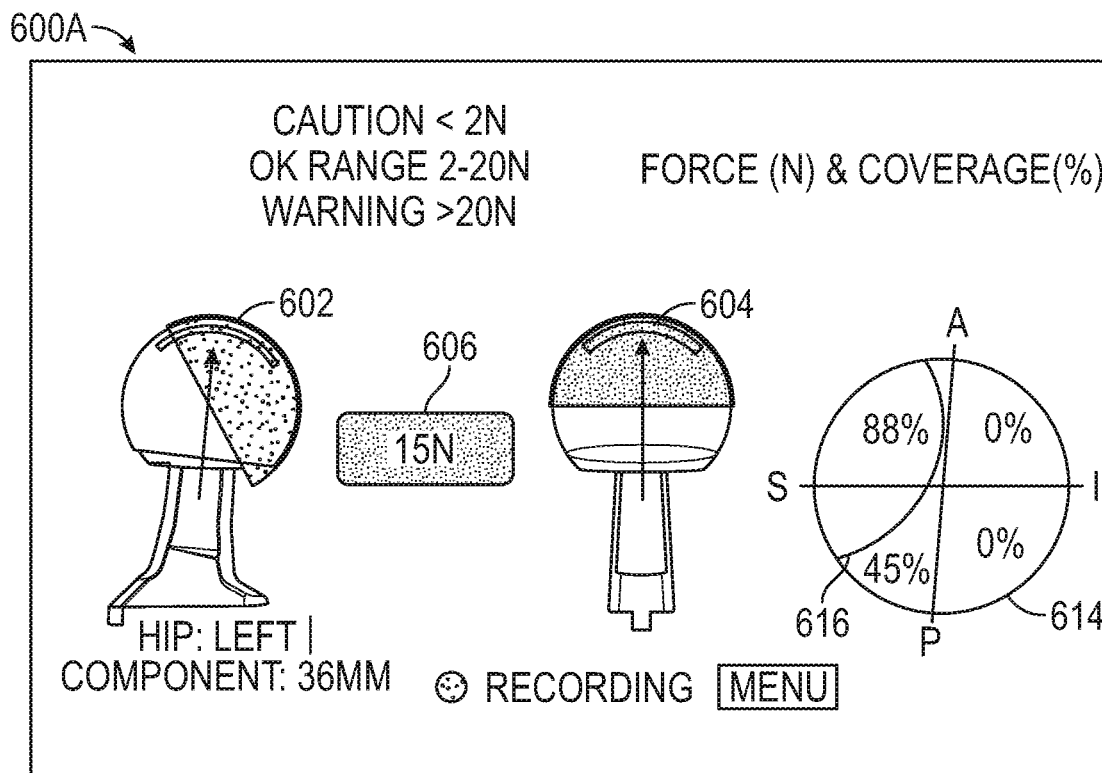
FIGS. 6A-6B illustrate user interfaces for displaying joint forces and proximity angles in accordance with some embodiments.
Figure 6B:
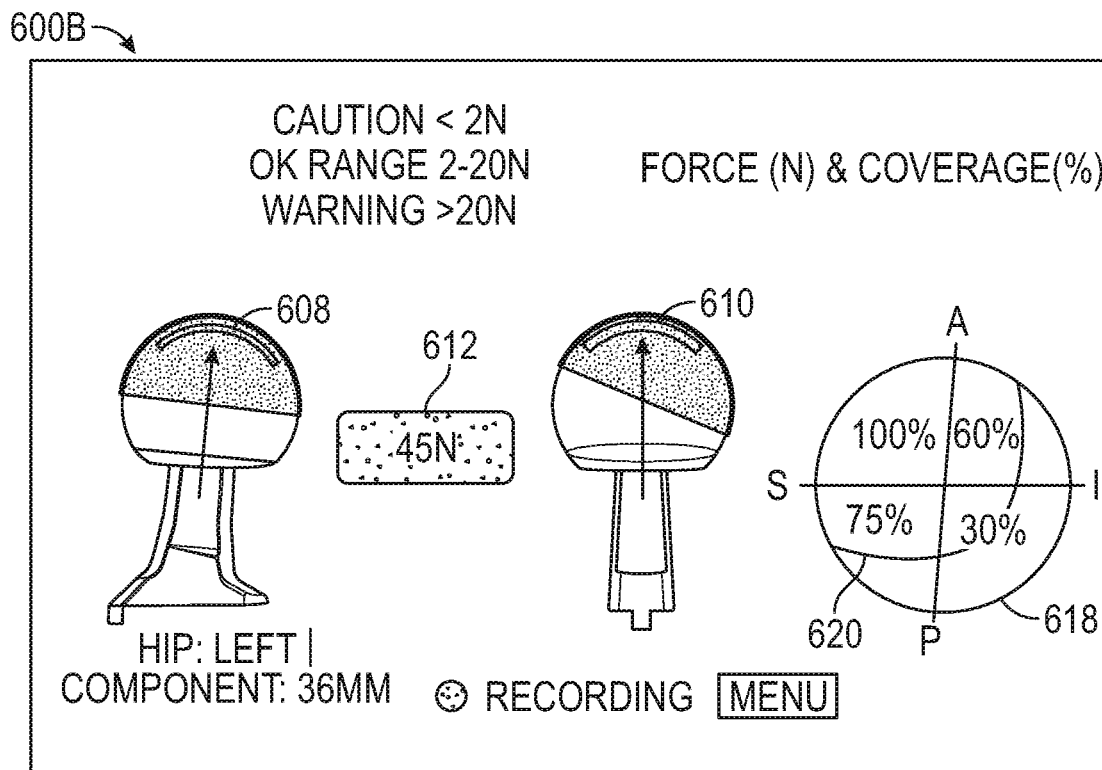

FIGS. 6A-6B illustrate user interfaces 600A and 600B for displaying joint forces and proximity angles in accordance with some embodiments. User interface 600A illustrates an example where an indication of impingement 602 is displayed. The indication of impingement 602 signifies that a first angle is outside a limit, such as a coverage proximity angle minimum or maximum (e.g., those selected on the user interface 500 of FIG. 5). For example, the angle limit may apply to inferior-superior (I-S) coverage or abduction-adduction coverage. A second indication 604 shows that a second angle limit has not been violated, such as a limit applied to anterior-posterior (A-P) coverage or flex-extension coverage. A force measurement 606 is also displayed. The force measurement 606 indicates that the force measured is within preset limits. In an example, the preset limits may be set using surgeon input, such as the joint force magnitude minimum and maximum established using the user interface 500 of FIG. 5. In another example, the preset limits may be set based on prior testing, experimentation, or manufacturing tolerances. The preset limits may include ranges, such as 0-10; 10-20; 20-30; 30-40; 40+, etc. The force measurement 606 may be measured by a force sensor integrated into the trunnion or a sensor force array (e.g., 5 sensors) integrated into the cup. These sensors may provide overall joint force and force distribution data.

The second angle 604 and the force measurement 606 are within tolerated limits, but the first angle 602 is outside the first angle limit, indicating a potential problem.

User interface 600A includes a range of motion top-down display that illustrates a location of a cup 616 with respect to a top-view of a cylindrical cross-section 614 of a joint. The cylindrical cross-section 614 may be broken down into quadrants, and each quadrant may include a percentage of coverage for a particular real-time assessment of range of motion of the cup 616. For example, the indication of impingement 602 may correspond to the lack of coverage for the two right quadrants (indicated by "0%"). In an example, the indication of impingement 602 may be triggered when one or more quadrants have a percentage below a threshold. In an example, impingement risk may be indicated in the indication of impingement 602 when an average of the two right quadrants or the two left quadrants falls below a threshold. The second indication 604 may be used to indicate a risk of impingement when an average of the top two quadrants or the bottom two quadrants falls below a threshold. In another example, a maximum of the top two or bottom two quadrants may be compared to a threshold to determine whether there is a risk of impingement in the A-P coverage. A maximum of the right two or left two quadrants may be compared to a threshold to determine whether there is a risk of impingement in the I-S coverage.

User interface 600B illustrates an example where a first indication 608 is displayed. The first indication 608 signifies that a first angle is within a limit, such as a coverage proximity angle minimum or maximum (e.g., those selected on the user interface 500 of FIG. 5). For example, the angle limit may apply to I-S coverage or abduction-adduction coverage. A second indication 610 shows that a second angle limit also has not been exceeded, such as a limit applied to A-P coverage or flex-extension coverage. A force measurement 612 is also displayed. The force measurement 612 indicates that the force measured is outside of preset limits (e.g., the joint force magnitude minimum and maximum established using the user interface 500 of FIG. 5). The first indication 608 and the second indication 610 are within tolerated limits, but the force measurement 612 is outside the force limit, indicating a potential problem. In an example, a potential problem may be indicated when any one of the two angles or the force are indicated as landing outside of tolerance limits.

The user interface 600B includes a second range of motion top-down display view that illustrates a location of a cup 620 in a second position (e.g., along a range of motion) with respect to a second top-view of a cylindrical cross-section 618 of a joint. The second range of motion view illustrates the cup 620 in coverage that mostly covers the cylindrical cross-section 618. For example, the quadrants from upper left to bottom left, clockwise, are 100%, 60%, 30%, and 75%. These quadrant coverage percentages may indicate that the risk of impingement is relatively low. For example, the first indication 608 and the second indication 610 may indicate that the coverage is proper and that there is a relatively low or no risk of impingement. The coverage indicated by the first indication 608 or the second indication 610 may correlate with whether one or more quadrants are above or below a threshold. For example, the first indication 608 may correspond with the left two or right two quadrants being, on average, for example, above a threshold.

In an example, angles of the cup (616 or 620) in relation to the cylindrical cross-section (614 or 618) may be interpreted as a coverage map or coverage percentage breakdown. For example, the orientation angles may create a centerline vector of the ball (with the cylindrical cross-section) within the cup. The cylinder of influence aligned to this vector may be plotted against a fixed circle to show the directional coverage of the ball within the cup.

The coverage concepts shown in FIGS. 600A-600B may be used to determine and display risks of impaction issues. When impacting a plastic liner into a fixed metal shell, a surgeon may not have a good idea of whether the impact is being hit by the impactor handle in a correct orientation to seat a component correctly. As a result, the impact may seat the component in a crooked orientation (e.g., not correctly oriented) and may need further impaction or correction. The sensors described above herein may be used to determine and display whether the alignment of the component is correct before or during impaction.

Figure 7:
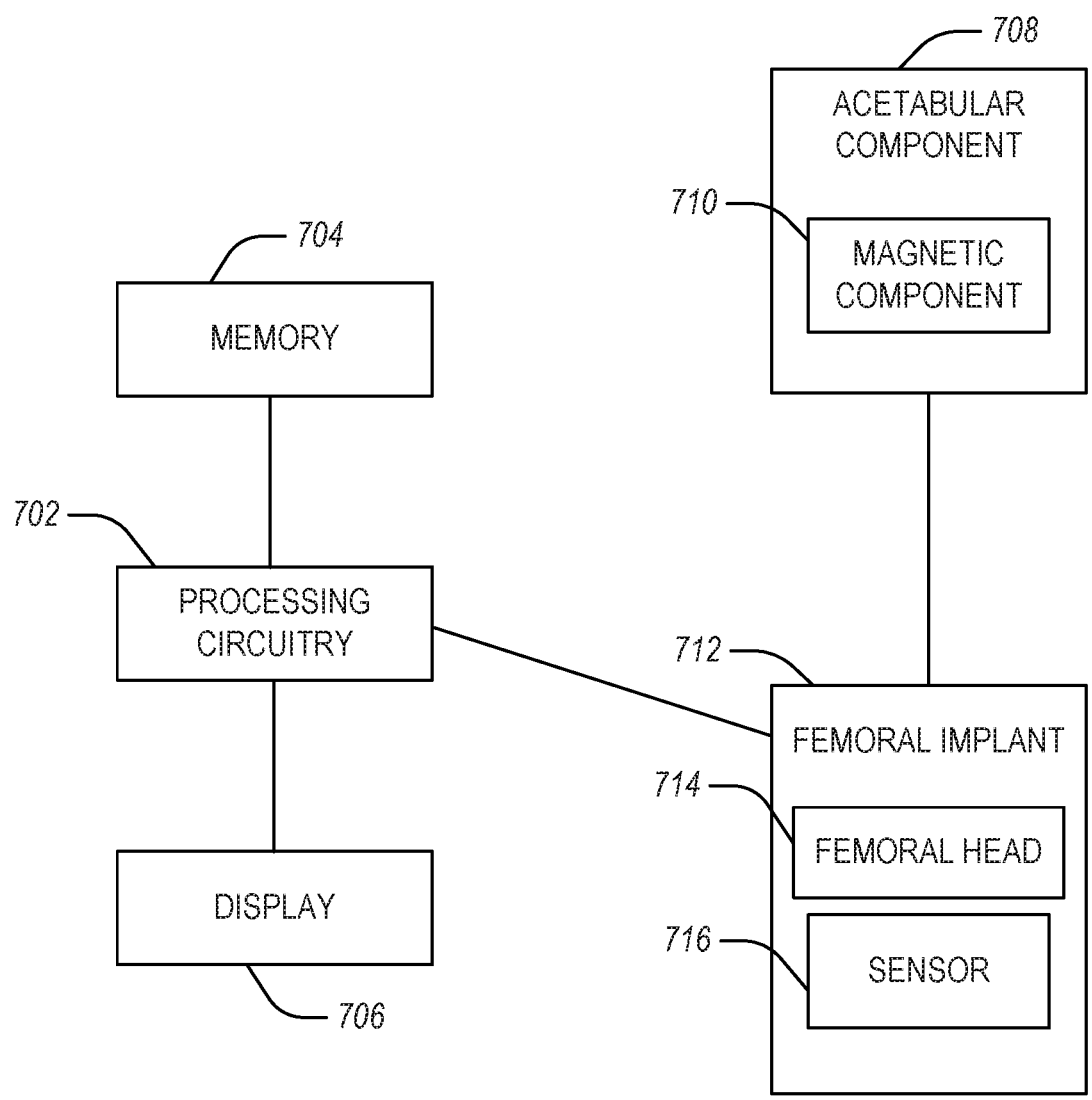
FIG. 7 illustrates a system for assessing hip arthroplasty component movement in accordance with some embodiments.

FIG. 7 illustrates a system 700 for assessing hip arthroplasty component movement in accordance with some embodiments. The system includes processing circuitry 702 coupled to memory 704 and a display 706. The processing circuitry 702 is in communication with a femoral implant 712 (e.g., a transceiver component of the femoral implant 712 or a sensor 716). The femoral implant 712 includes the sensor 716 and a femoral head 714. The femoral head 714 is configured to fit within an acetabular component 708. The acetabular component 708 includes a magnetic component 710, such as a plurality of magnets or a magnetic ring. The acetabular component may include a cup liner or a shell.

In an example, the magnetic component 710 emits a magnetic field. The sensor 716 of the femoral implant 712 may be used to detect the magnetic field. The processing circuitry 702 may be used to receive information from the sensor 716 about the magnetic field. The processing circuitry 702 may be used to output an indication of a fit of the femoral head 714 in the acetabular component 708. The indication may include an angle (e.g., potential impingement), a risk of impingement, a force exerted by the femoral head 714 on the acetabular component 708, an insertion measurement, a risk factor for dislocation, a risk-level for postoperative impingement, a patient-specific assessment of alignment of the acetabular component 708 (e.g., with respect to the femoral head 714), or the like. The processing circuitry 702 may output the indication using the display 706. The display 706 may include a heads-up display (e.g., projected on a surgical drape, a patient, goggles, glasses, etc.), an augmented reality display (e.g., using glasses, goggles, etc.), a display screen (e.g., a computer monitor, a mobile device, etc.), or the like. In another example, the processing circuitry 702 may output the indication using an audible alert, haptic feedback, or the like.

In an example, the information from the sensor may include a voltage based on proximity of the sensor 716 to the magnetic field. The voltage may be directly proportional to a strength of the magnetic field. The processing circuitry 702 may receive, prior to receiving the information, predefined impingement criteria, such as a joint force magnitude limit or a low limit proximity angle. In an example, the impingement criteria may include preoperative set points, such as to establish a level of insertion. In an example, the indication may include a visual indication of impingement or lack of impingement based on the preoperative set points and the magnetic field.

In an example, the sensor 716 includes a Hall effect sensor, a reed switch, a proximity sensor, a magnetometer, or the like. In an example, the femoral implant 712 may include a plurality of sensors, for example, arranged in two intersecting arcs on within the femoral head 714, arranged in a grid on or within the femoral head 714, arranged in circles (e.g., concentric circles or rings at different heights of the femoral head 714), etc. In another example, the sensor 716 may be embedded in a trunnion of the femoral implant 712. In an example, the system 700 may be pre-calibrated during manufacturing, so as to allow a surgeon to plug-and-play the system 700.

Figure 8:
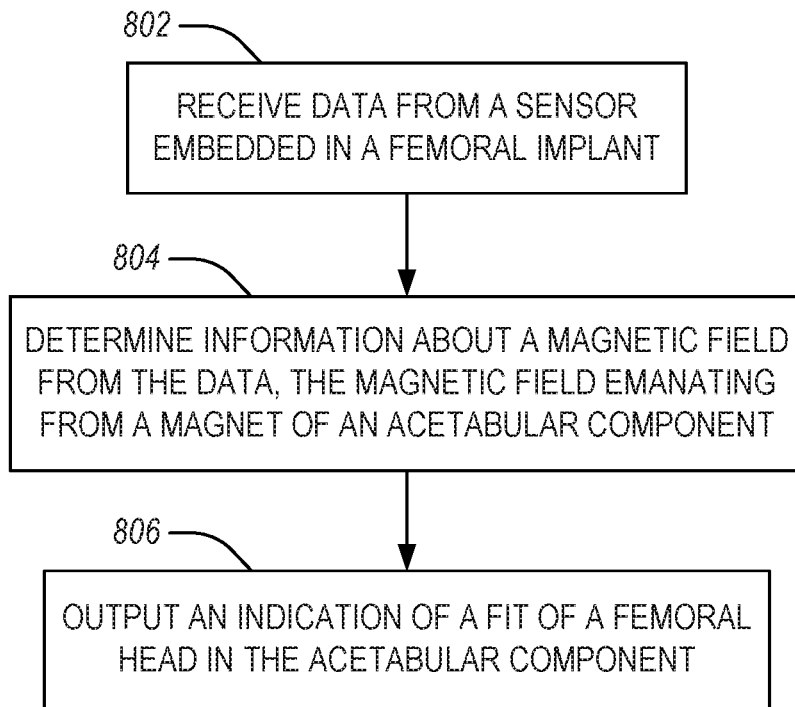
FIG. 8 illustrates a flow chart showing a technique for assessing hip arthroplasty component movement in accordance with some embodiments.

FIG. 8 illustrates a flow chart showing a technique 800 for assessing hip arthroplasty component movement in accordance with some embodiments. The technique 800 includes an operation 802 to receive data from a sensor embedded in a femoral implant, such as in a trunnion of the femoral implant or in a femoral head of the femoral implant. The femoral head may be configured to fit in an acetabular component. The technique 800 includes an operation 804 to determine information about a magnetic field from the data, the magnetic field emanating from a magnet of the acetabular component.

The technique 800 includes an operation 806 to output an indication of a fit of a femoral head in the acetabular component, a combined version angle, a proximity, a coverage percentage, or the like. The indication may include an angle (e.g., potential impingement), a risk of impingement, a force exerted by the femoral head on the acetabular component, an insertion measurement, a risk factor for dislocation, a risk-level for postoperative impingement, a patient-specific assessment of alignment of the acetabular component (e.g., with respect to the femoral head), or the like. The technique 800 may include outputting the indication using a heads-up display (e.g., projected on a surgical drape, a patient, goggles, glasses, etc.), an augmented reality display (e.g., using glasses, goggles, etc.), a display screen (e.g., a computer monitor, a mobile device, etc.), an audible alert, haptic feedback, non-contact indications, or the like.

Figure 9:
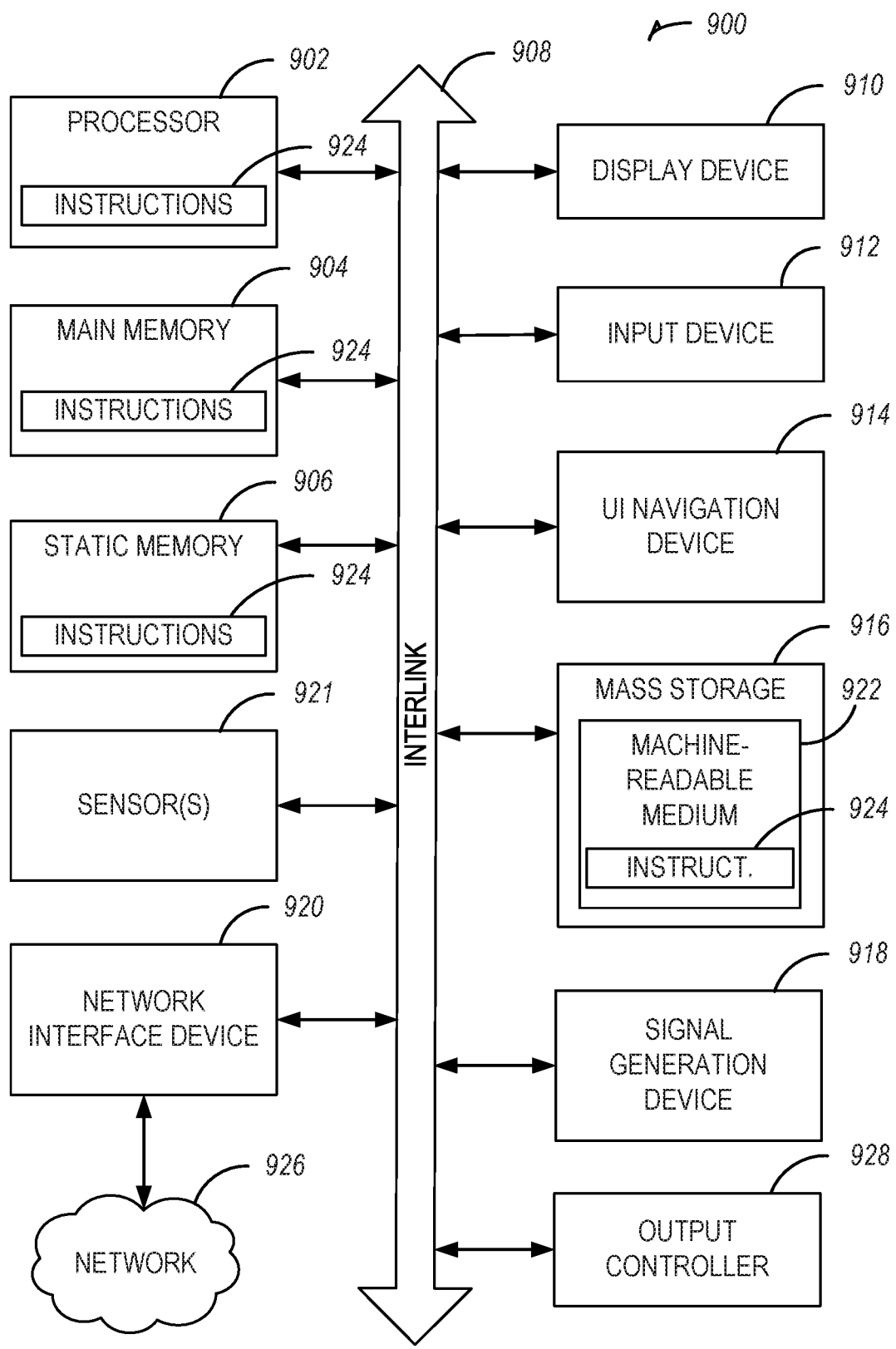
FIG. 9 illustrates generally an example of a block diagram of a machine upon which any one or more of the techniques discussed herein may perform in accordance with some embodiments.

FIG. 9 illustrates generally an example of a block diagram of a machine 900 upon which any one or more of the techniques (e.g., methodologies) discussed herein may perform in accordance with some embodiments. In alternative embodiments, the machine 900 may operate as a standalone device or may be connected (e.g., networked) to other machines. In a networked deployment, the machine 900 may operate in the capacity of a server machine, a client machine, or both in server-client network environments. The machine 900 may be a personal computer (PC), a tablet, a personal digital assistant (PDA), a mobile telephone, a web appliance, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate on, logic or a number of components, modules, or like mechanisms. Such mechanisms are tangible entities (e.g., hardware) capable of performing specified operations when operating. In an example, the hardware may be specifically configured to carry out a specific operation (e.g., hardwired). In an example, the hardware may include configurable execution units (e.g., transistors, circuits, etc.) and a computer readable medium containing instructions, where the instructions configure the execution units to carry out a specific operation when in operation. The configuring may occur under the direction of the executions units or a loading mechanism. Accordingly, the execution units are communicatively coupled to the computer readable medium when the device is operating. For example, under operation, the execution units may be configured by a first set of instructions to implement a first set of features at one point in time and reconfigured by a second set of instructions to implement a second set of features.

Machine (e.g., computer system) 900 may include a hardware processor 902 (e.g., a central processing unit (CPU), a graphics processing unit (GPU), a hardware processor core, any combination thereof, or other processing circuitry), a main memory 904 and a static memory 906, some or all of which may communicate with each other via an interlink (e.g., bus) 908. The machine 900 may further include a display unit 910, an alphanumeric input device 912 (e.g., a keyboard), and a user interface (UI) navigation device 914 (e.g., a mouse). In an example, the display unit 910, alphanumeric input device 912 and UI navigation device 914 may be a touch screen display. The machine 900 may additionally include a storage device (e.g., drive unit) 916, a signal generation device 918 (e.g., a speaker), a network interface device 920, and one or more sensors 921, such as a global positioning system (GPS) sensor, compass, accelerometer, or other sensor. The machine 900 may include an output controller 928, such as a serial (e.g., universal serial bus (USB), parallel, or other wired or wireless (e.g., infrared (IR), near field communication (NFC), etc.) connection to communicate or control one or more peripheral devices.

The storage device 916 may include a machine readable medium 922 that is non-transitory on which is stored one or more sets of data structures or instructions 924 (e.g., software) embodying or utilized by any one or more of the techniques or functions described herein. The instructions 924 may also reside, completely or at least partially, within the main memory 904, within static memory 906, or within the hardware processor 902 during execution thereof by the machine 900. In an example, one or any combination of the hardware processor 902, the main memory 904, the static memory 906, or the storage device 916 may constitute machine readable media.

While the machine readable medium 922 is illustrated as a single medium, the term "machine readable medium" may include a single medium or multiple media (e.g., a centralized or distributed database, or associated caches and servers) configured to store the one or more instructions 924.

The term "machine readable medium" may include any medium that is capable of storing, encoding, or carrying instructions for execution by the machine 900 and that cause the machine 900 to perform any one or more of the techniques of the present disclosure, or that is capable of storing, encoding or carrying data structures used by or associated with such instructions. Non-limiting machine readable medium examples may include solid-state memories, and optical and magnetic media. Specific examples of machine readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 924 may further be transmitted or received over a communications network 926 using a transmission medium via the network interface device 920 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi® or IEEE 802.15.4 family of standards known as ZigBee)), as the personal area network family of standards known as Bluetooth® that are promulgated by the Bluetooth Special Interest Group, peer-to-peer (P2P) networks, among others. In an example, the network interface device 920 may include one or more physical jacks (e.g., Ethernet, coaxial, or phone jacks) or one or more antennas to connect to the communications network 926. In an example, the network interface device 920 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 900, and includes digital or analog communications signals or other intangible medium to facilitate communication of such software.

Figure 10:
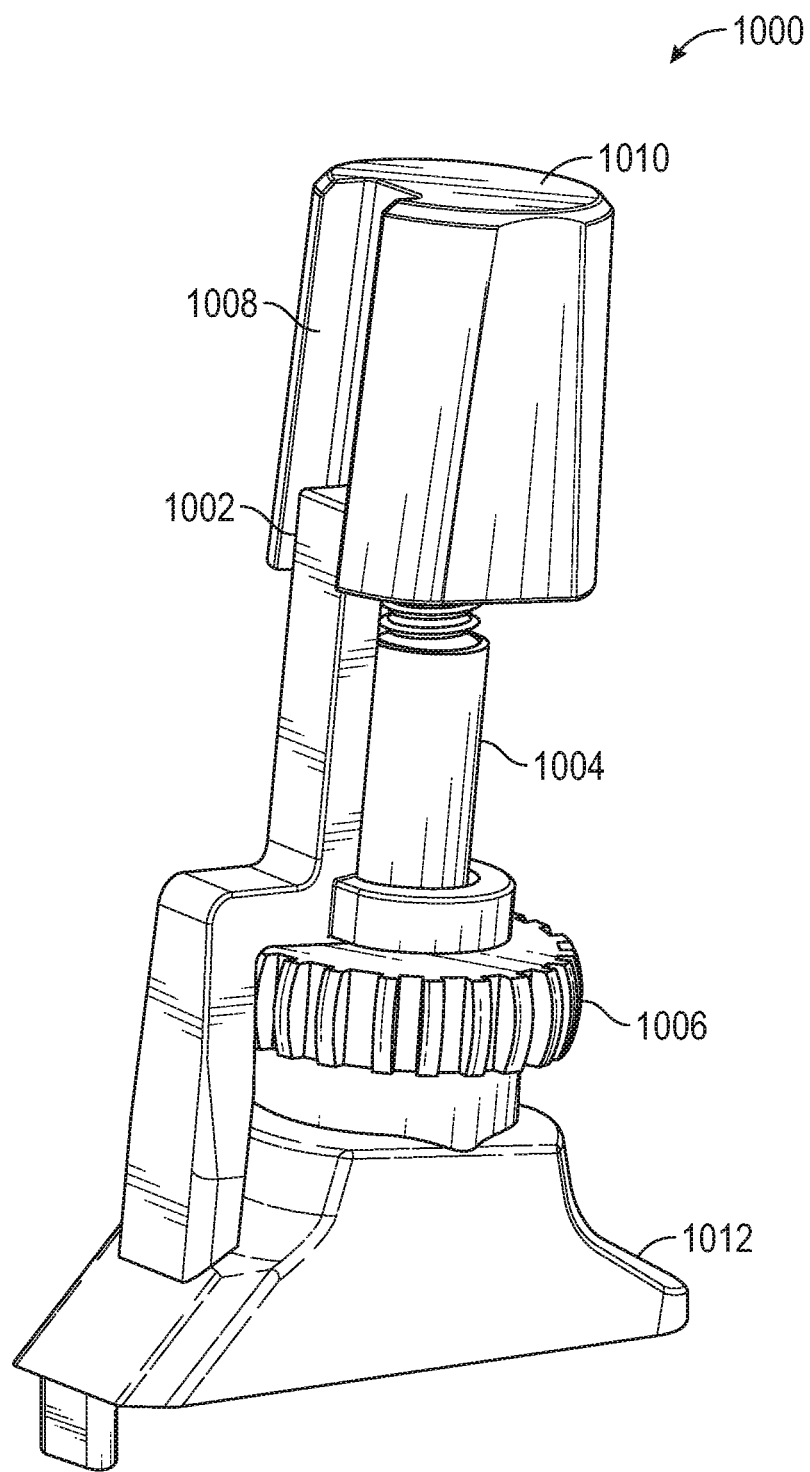
FIG. 10 illustrates an adjustable trunnion in accordance with some embodiments.

FIG. 10 illustrates an adjustable trunnion 1000 in accordance with some embodiments. A trunnion may include a support shaft, such as a femoral stem, which may be inserted into a femoral head component. The adjustable trunnion 1000 includes a guide 1002, which may travel along a groove 1008 of a trunnion head 1010 of the adjustable trunnion 1000. The trunnion head 1010 may be configured to receive a femoral head component (e.g., as described below with respect to FIG. 11). In an example, the guide 1002 may allow the adjustable trunnion 1000 to expand up to 12 millimeters of total height in this example. Different expansion heights are within the scope of the present disclosure. By allowing the adjustable trunnion 1000 to change heights, a single femoral head component may be used with the adjustable trunnion 1000 instead of requiring multiple different trial sizes for the femoral head component.

The adjustable trunnion 1000 may be adjusted using a height controller 1006. In an example, the height controller 1006 may be hand-adjustable or tool-adjustable. For example, the height controller 1006 may include a turning mechanism to allow a surgeon to turn the height controller 1006 with a hand to apply a torque, causing an adjustable shaft 1004 to increase or decrease in height (e.g., a distance between the trunnion head 1010 and a base component 1012 of the adjustable trunnion 1000). In another example, the height controller 1006 may be adjusted by a tool (e.g., a wrench), which may include a powered component. In an example, the adjustable shaft 1004 may include a lead screw mechanism. In yet another example, the height controller 1006 may be electronically controlled to adjust the height of the adjustable trunnion 1000 (e.g., receiving an electrical signal may cause the adjustable shaft 1004 to increase or decrease in height). In this example, the adjustable trunnion 1000 may be motorized to cause the adjustment. In certain examples, a wireless controller may control adjustment height of a powered adjustable trunnion 1000. In another example, an optical encoder may be used to control adjustment of the height or accurately determine height after adjustment.

In an example, the adjustable trunnion 1000 may be used with a single trial reduction. The adjustable trunnion 1000 may be dynamically adjusted while a joint force is monitored. In another example, the adjustable trunnion 1000 may be dynamically adjusted using a leg length sensor to automatically determine a height fit. In an example, the adjustable trunnion 1000 may be reusable. In an example, the femoral component is a trial component. In an example, the acetabular component is a standard implant selected from a standard set of implants provided by an implant manufacturer (e.g., does not include a sensor or does not include a magnet, or both).

In an example, the adjustable trunnion 1000 may not include any magnets or sensors. In another example, a magnet may be deployed within the adjustable trunnion 1000, for example, within the guide 1002. The magnet within the guide 1002 may be used to determine a height or an offset amount. The height may be sent to a graphical user interface (e.g., those described with respect to FIGS. 5 and 6A-6B) for display. The height determined using the magnet may be used to perform preoperative planning, for example, to determine a proper leg length for an implant. In an example, the height may be used intraoperatively, such as to monitor a force on the adjustable trunnion 1000. In an example, the magnet within the guide 1002 may be magnetically small enough to avoid interfering with a hall effect sensor or a magnetometer or other magnets within a femoral head component. In another example, the magnet within the guide 1002 may be used to calibrate a hall effect sensor, a magnetometer, or another sensor or magnet within the femoral head component.

Figure 11:
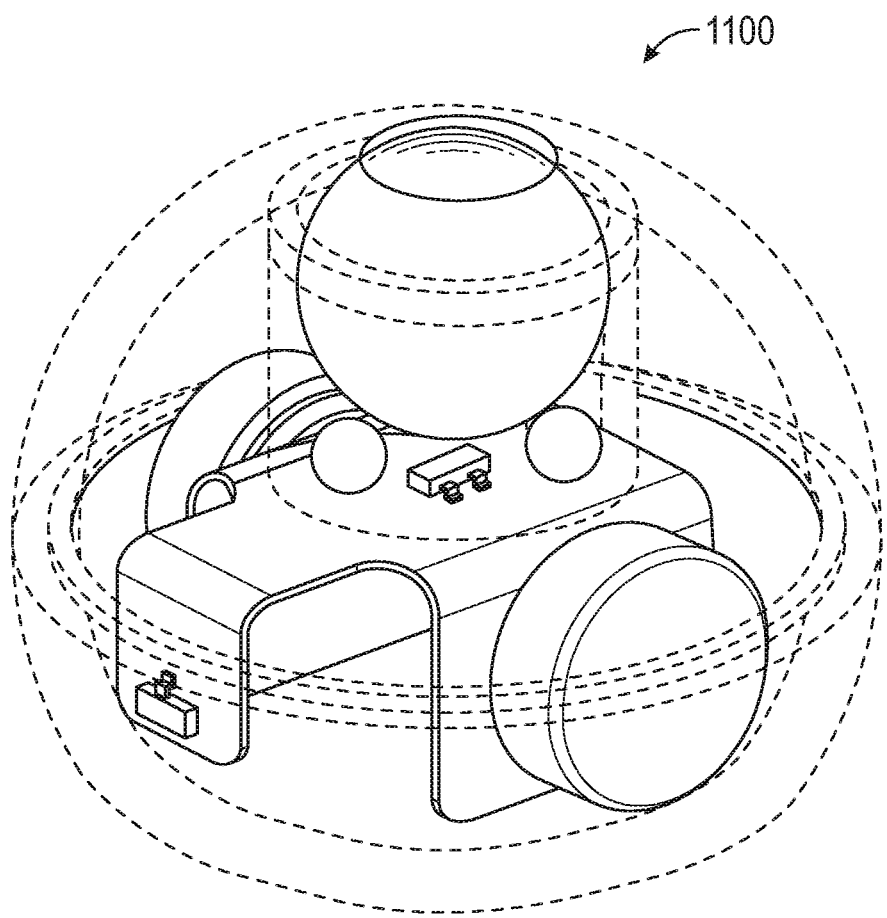
FIG. 11 illustrates an assembled view of a femoral head component in accordance with some embodiments.

FIG. 11 illustrates an assembled view of a femoral head component 1100 in accordance with some embodiments. In an example, the femoral head component 1100 may be coupled with the adjustable trunnion 1000 of FIG. 10 to create a single-use femoral sensor trial. In an example, the femoral head component 1100 may be customized to a patient, and disposable after a single use. The femoral head component 1100 may include a three-dimensional (3D) magnetometer. The 3D magnetometer may be located within the femoral head component 1100, and may be used to provide a position or orientation of the femoral head component 1100, such as with respect to a cup (e.g., an acetabular cup), for example without receiving information from the cup. The magnetometer within the femoral head component 1100 may be compatible with any manufactured cup, rather than requiring a paired cup component (e.g., as shown in FIGS. 2A-2C and 3A-3D). In an example, the femoral head component 1100 may have a standard diameter size, such as 22 mm, 28 mm, 32 mm, 36 mm, etc.

Figure 12:
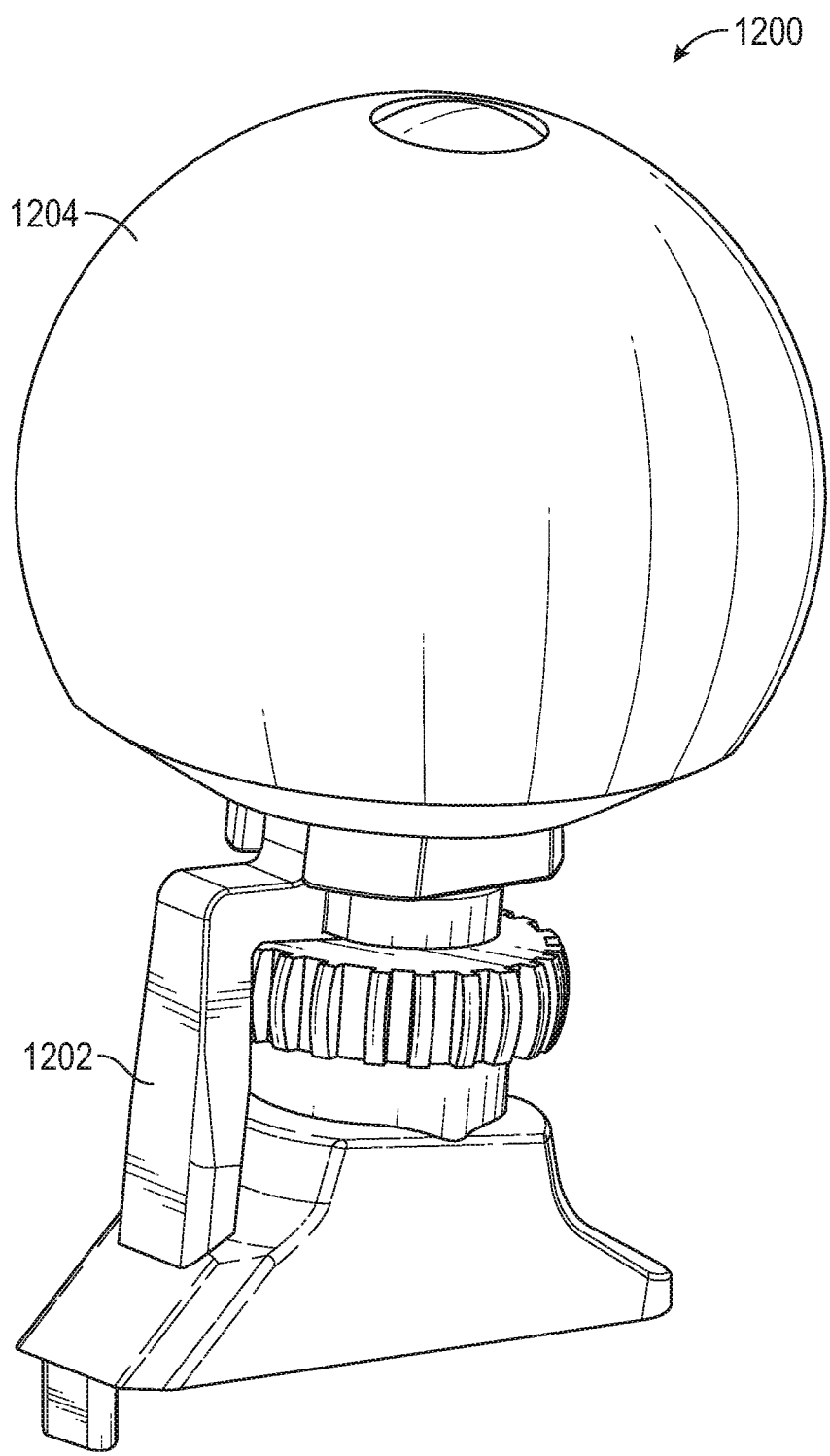
FIG. 12 illustrates a combined adjustable trunnion and femoral head component system in accordance with some embodiments.

FIG. 12 illustrates a combined adjustable trunnion 1202 and femoral head component 1204 system 1200 in accordance with some embodiments. The adjustable trunnion 1202 may be used with a single sized-fits-all femoral head component 1204. For example, by allowing for changes within the adjustable trunnion 1202 for height of the adjustable trunnion 1202, the femoral head component 1204 may change location based on a shaft of the femoral head component 1204 that fits over a head portion of the adjustable trunnion 1202. The height adjustments allow for the femoral head component 1204 to be used in different patients without needing to change the diameter of the femoral head component 1204. For example, one current system uses eight different femoral head component sizes with two different trunnion options. The combined adjustable trunnion 1202 and femoral head component 1204 system 1200 described herein allows for a single femoral head component 1204 with different heights controlled using a single adjustable trunnion 1202.

Figure 13:
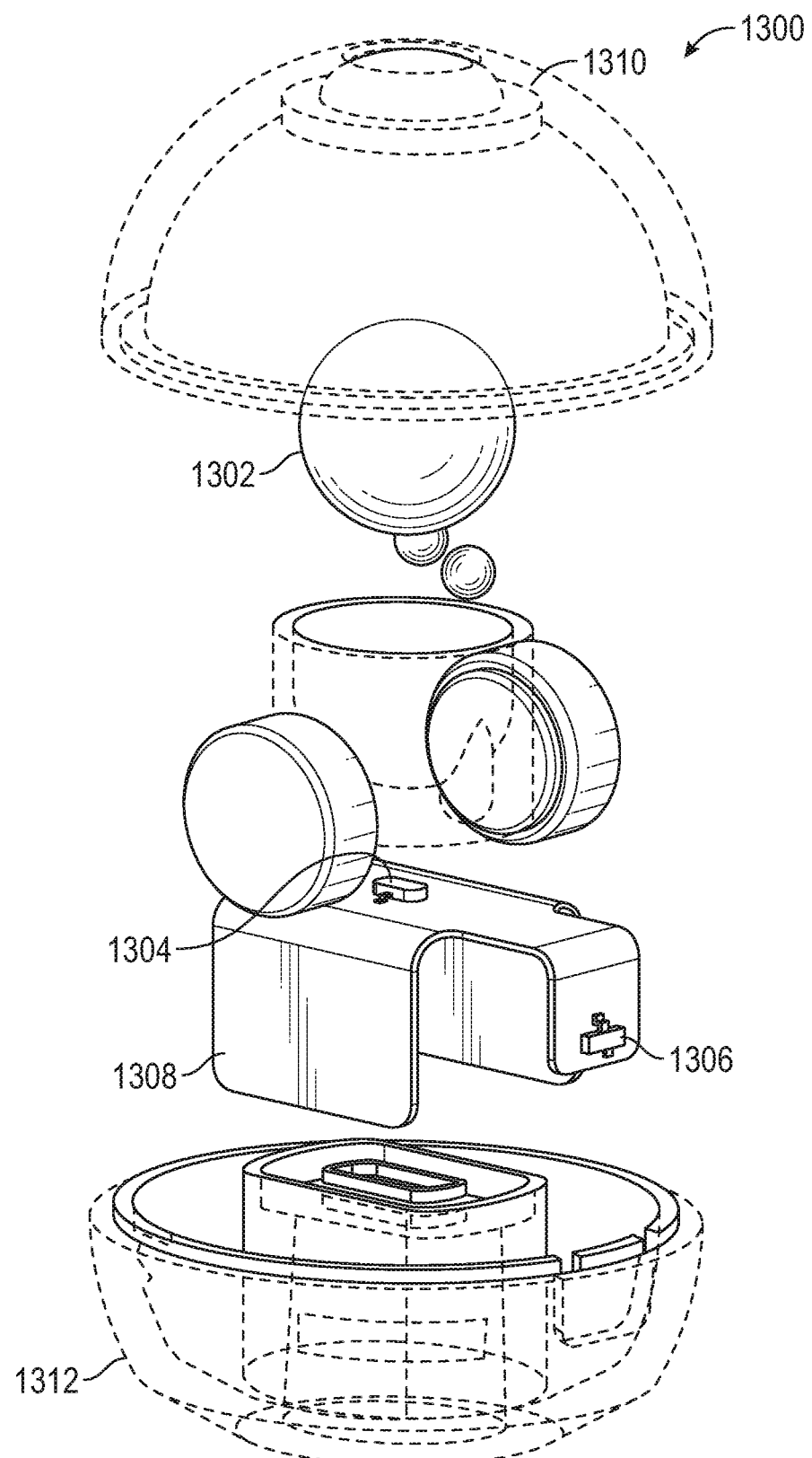
FIG. 13 illustrates an exploded view of a femoral head component in accordance with some embodiments.

FIG. 13 illustrates an exploded view of a femoral head component 1300 in accordance with some embodiments. The femoral head component 1300 may include a tracking ball or magnetic sphere 1302, a 3D magnetometer 1304, a 2D hall effect sensor 1306, and a printed circuit board (PCB)/battery assembly 1308. The PCB/battery assembly 1308 may include control circuitry to control the magnetometer 1304, the hall effect sensor 1306, or the like. The PCB/battery assembly 1308 may include a battery to power the magnetometer 1304, the hall effect sensor 1306, or the like. For example, the PCB/battery assembly 1308 may be used to initialize the hall effect sensor 1306 or the magnetometer 1304. The PCB/battery assembly 1308 may include a transceiver or other communication device for sending information to a remote device (e.g., a computer, a tablet, a mobile device, etc.), such as magnetometer information. For example, the transceiver or other communication device may send magnetometer information for displaying an angle of the femoral head component 1300, for example with respect to an acetabular component (e.g., as shown and described with respect to FIG. 6A-6B or 15).

The femoral head component 1300 may include a cap component 1310 and a base component 1312. The cap component 1310 may be configured to couple with the base component 1312, such as using tension to prevent decoupling. The base component 1312 may be configured to include a groove, slot, or aperture, such as to receive a head portion of a trunnion (e.g., the adjustable trunnion of FIG. 10 or 12).

In an example, the magnetometer 1304 may include a plurality of magnetometers in an array. The magnetometer 1304 may be used to determine a relative tilt or angle of the femoral head component 1300 or rotation of the femoral head component 1300. The hall effect sensor 1306 may be used to calibrate the magnetometer 1304 with the tracking ball or magnetic sphere 1302 or the cap component 1310. For example, the hall effect sensor 1306 may be initialized (e.g., using the PCB/battery assembly 1308 or an external button or controller. At initialization, the femoral head component 1300 may be held in a position representing an origin or zero location using the hall effect sensor 1306. An output magnetic field may be read from the magnetometer 1304 at the origin or zero location. When the femoral head component 1300 is moved, a new output magnetic field reading from the magnetometer 1304 may be compared to the origin or zero location reading to determine a change in magnetic field. The change in magnetic field may be used to determine an angle of the femoral head component 1300, such as with respect to an acetabular component.

Figure 14:
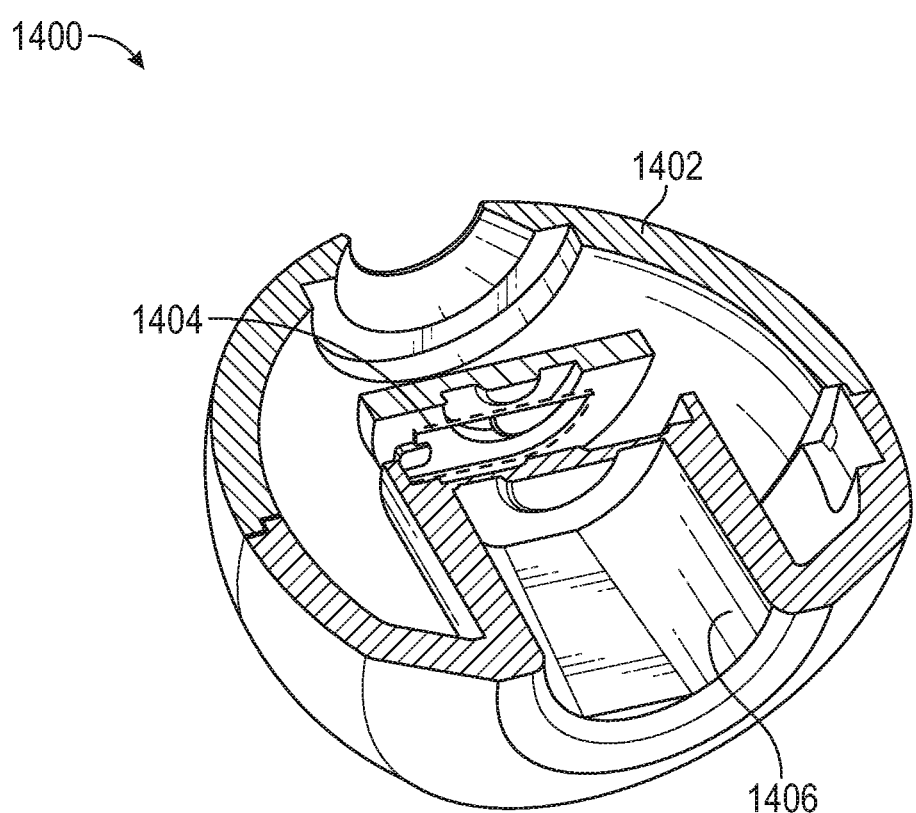
FIG. 14 illustrates a sectional view of a portion of a femoral head component in accordance with some embodiments.

FIG. 14 illustrates a sectional view 1400 of a portion of a femoral head component 1402 in accordance with some embodiments. The portion of the femoral head component 1402 includes a groove 1406, for example to receive a portion of a trunnion (e.g., the adjustable trunnion of FIG. 10 or 12). The portion of the femoral head component 1402 includes a force sensor 1404. In an example, the force sensor 1404 may detect load transferred through the femoral head component 1402 into a trunnion (e.g., the adjustable trunnion of FIG. 10 or 12). A force measured by the force sensor 1404 may be used to determine an offset selection (e.g., a height of the adjustable trunnion). In an example, the force measured by the force sensor 1404 may be used to detect impingement or subluxation, for example, when the force is zero. In an example, the force measured by the force sensor 1404 may be used to detect a high or an unusual load, such as during a range of motion test. The force measured by the force sensor 1404 may be output, such as on the graphical user interface 1500 of FIG. 15.

Figure 15:
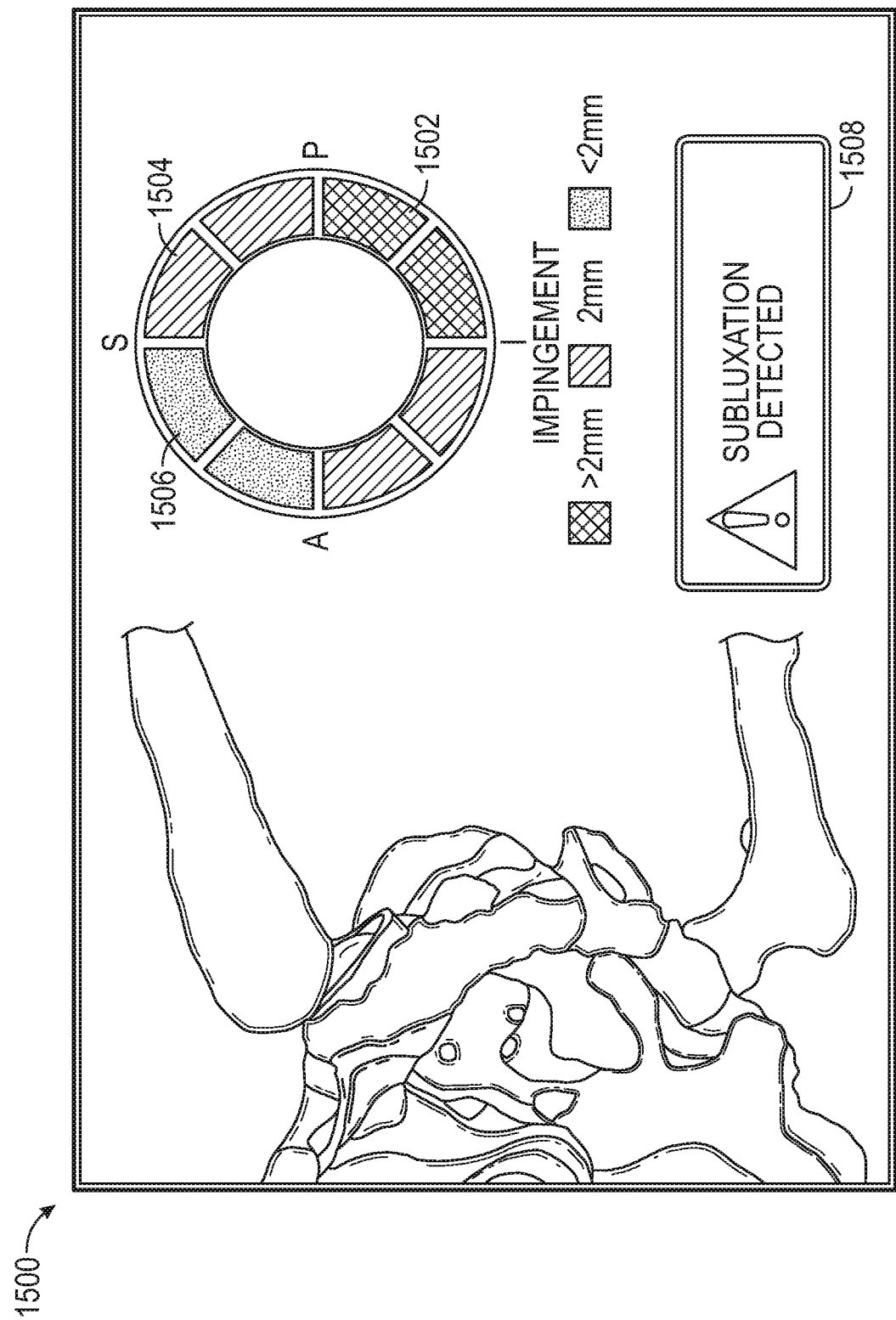
FIG. 15 illustrates a graphical user interface for displaying impingement information in accordance with some embodiments.

FIG. 15 illustrates a graphical user interface 1500 for displaying impingement information (e.g., at user interface elements 1502, 1504, 1506, or 1508), force information, or range of motion information in accordance with some embodiments. In the example shown in FIG. 15, the user interface element 1502 illustrates a lack of impingement (e.g., less than 2 millimeter impingement) at the inferior-posterior quadrant. The user interface element 1504 illustrates a potential impingement (e.g., 2 millimeter impingement) at the superior-posterior quadrant (also seen at the inferior-anterior quadrant). The user interface element 1506 illustrates impingement (e.g., greater than 2 millimeter impingement) at the superior-anterior quadrant. The user interface element 1506 illustrates a subluxation warning when subluxation is detected indicating impingement. The graphical user interface 1500 may be displaying range of motion, force, or impingement information, such as during a range of motion test.

Figure 16:
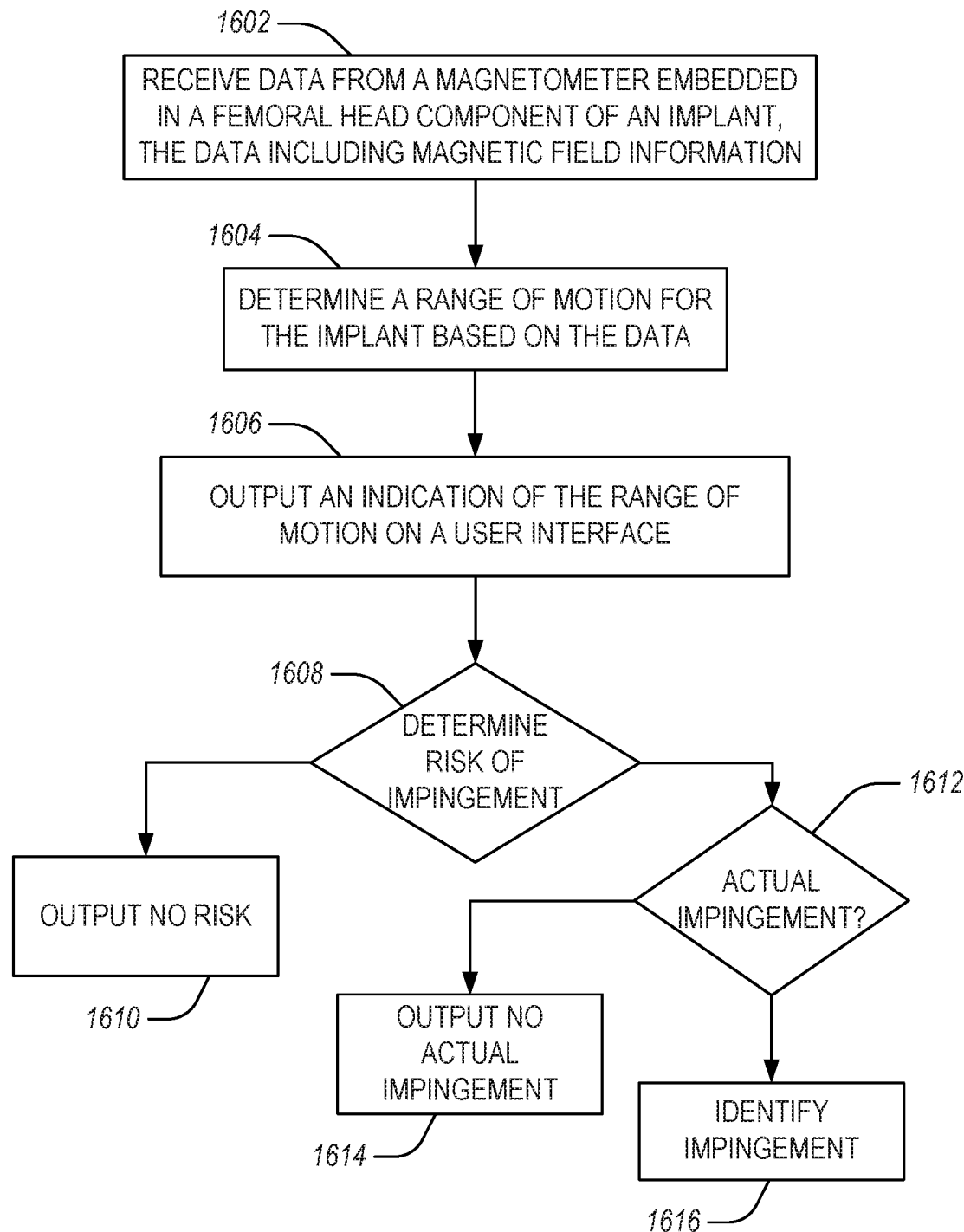
FIG. 16 illustrates a flow chart showing a technique for outputting impingement information in accordance with some embodiments.

FIG. 16 illustrates a flow chart showing a technique 1600 for outputting impingement information in accordance with some embodiments. The technique 1600 includes an operation 1602 to receive data from a magnetometer embedded in a femoral head component of an implant, the data including magnetic field information. The technique 1600 includes an operation 1604 to determine a range of motion for the implant based on the data. The technique 1600 includes an operation 1606 to output an indication of the range of motion on a graphical user interface. The technique 1600 includes an decision operation 1608 to determine whether there is a risk of impingement. In an example, determining risk of impingement may be performed before, during, after, or in replacement of, determining a range of motion.

In response to determining that there is no risk of impingement, the technique 1600 includes an operation 1610 to output that there is no risk of impingement. In response to determining that there is a potential risk of impingement, the technique 1600 may include an operation to output that there is a risk of impingement. In response to determining that there is a potential risk of impingement, the technique 1600 includes a decision operation 1612 to determine whether there is an actual impingement. In another example, actual impingement may be tested separately from risk of impingement or may be tested before testing for risk of impingement. In response to determining that there is no actual impingement at decision operation 1612, the technique 1600 includes outputting that there is no actual impingement at operation 1614. In response to determining that there is actual impingement, the technique 1600 includes an operation 1616 to output impingement information, such as by identifying a location on the femoral head (e.g., using a GUI), that impingement has occurred.

VARIOUS NOTES & EXAMPLES

Each of these non-limiting examples may stand on its own, or may be combined in various permutations or combinations with one or more of the other examples.

Example 1 is a system for assessing orientation and dynamics of a hip arthroplasty component, the system comprising: an acetabular component including a magnetic component to emit a magnetic field; a femoral component including: a femoral head configured to be accommodated by the acetabular component; and a sensor to detect the magnetic field; and processing circuitry to: receive information from the sensor about the magnetic field; determining a relative orientation of the femoral component with respect to the acetabular component based at least in part on the information received from the sensor; and output an indication based on the relative orientation.

In Example 2, the subject matter of Example 1 includes, wherein the sensor is a Hall effect sensor and the information from the sensor includes a measured voltage based on proximity of the sensor to the magnetic field.

In Example 3, the subject matter of Example 2 includes, wherein the measured voltage is directly proportional to a strength of the magnetic field.

In Example 4, the subject matter of Examples 1-3 includes, wherein the processing circuitry is further to receive predefined criteria including impingement criteria, joint force criteria, or an orientation angle prior to receiving the information.

In Example 5, the subject matter of Example 4 includes, wherein the predefined criteria includes a lower or upper magnitude limit for each of the predefined criteria.

In Example 6, the subject matter of Examples 4-5 includes, wherein the joint force criteria, the orientation angle, or the impingement criteria includes preoperative set points.

In Example 7, the subject matter of Example 6 includes, wherein the indication includes a visual indication of impingement or lack of impingement based on a comparison between the preoperative set points and the relative orientation.

In Example 8, the subject matter of Examples 1-7 includes, wherein the indication includes a coverage of the femoral component over the acetabular component and a force imparted by the femoral component on the acetabular component.

In Example 9, the subject matter of Examples 1-8 includes, wherein the sensor includes at least one of a Hall effect sensor, a reed switch, a proximity sensor, or a magnetometer.

In Example 10, the subject matter of Examples 1-9 includes, wherein the sensor includes a plurality of sensors arranged in two intersecting arcs within the femoral head.

In Example 11, the subject matter of Examples 1-10 includes, wherein the sensor is embedded in a trunnion of the femoral component.

In Example 12, the subject matter of Examples 1-11 includes, wherein the magnetic component is removable from the acetabular component.

In Example 13, the subject matter of Examples 1-12 includes, wherein the magnetic component is a magnetic ring.

In Example 14, the subject matter of Examples 1-13 includes, wherein to output the indication, the processing circuitry is to output the indication using a heads-up display, an augmented reality display, or a display screen.

In Example 15, the subject matter of Examples 1-14 includes, wherein the indication includes a risk-level for postoperative impingement or an alert of an impingement.

In Example 16, the subject matter of Examples 1-15 includes, wherein the indication includes a patient-specific assessment of alignment of the acetabular component including the relative orientation.

Example 17 is a method for assessing orientation or dynamics of a hip arthroplasty component, the method comprising: receiving, at processing circuitry, data from a sensor embedded in a femoral component, the femoral component including a femoral head configured to be accommodated by an acetabular component; determining, at the processing circuitry, information about a magnetic field from the data, the magnetic field emanating from a magnetic component integrated with the acetabular component; and outputting, from the processing circuitry, an indication indicative of a relative orientation of the femoral component with respect to the acetabular component based on the information about the magnetic field.

In Example 18, the subject matter of Example 17 includes, wherein the indication includes a risk-level for postoperative impingement or an alert of an impingement.

Example 19 is at least one machine-readable medium including instructions for assessing orientation or dynamics of a hip arthroplasty component that, when executed by a machine, cause the machine to: receive data from a sensor embedded in a femoral component, the femoral component including a femoral head configured to be accommodated by an acetabular component; determine information about a magnetic field from the data, the magnetic field emanating from a magnetic component integrated with the acetabular component; and output an indication indicative of a relative orientation of the femoral component with respect to the acetabular component, the indication based at least in part on the information about the magnetic field.

In Example 20, the subject matter of Example 19 includes, wherein the indication includes a patient-specific assessment of alignment of the acetabular component including a visual indication of the relative orientation.

Example 21 is a system for assessing orientation and dynamics of a hip arthroplasty component, the system comprising: a femoral head component including: a magnetometer to: obtain initial magnetic field information; and obtain updated magnetic field information when the femoral head component is moved during a range of motion test; and a hall effect sensor to: register an initial orientation based on the initial magnetic field information; and a processor to: determine a relative orientation of the femoral head component in reference to an acetabular component based on a change between the initial and the updated magnetic field information using the initial orientation; and output an indication based on the relative orientation.

In Example 22, the subject matter of Example 21 includes, wherein the processor is further to receive, prior to receiving the information, predefined criteria including impingement criteria, joint force criteria, or an orientation angle.

In Example 23, the subject matter of Example 22 includes, wherein the predefined criteria includes a lower or upper magnitude limit for each of the predefined criteria.

In Example 24, the subject matter of Examples 22-23 includes, wherein the joint force criteria, the orientation angle, or the impingement criteria includes preoperative set points.

In Example 25, the subject matter of Example 24 includes, wherein the processor is further to output a visual indication of impingement or lack of impingement based on the preoperative set points and the relative orientation.

In Example 26, the subject matter of Examples 21-25 includes, wherein the femoral head component further includes a force sensor to detect a force imparted on the femoral head component by a trunnion at the relative orientation.

In Example 27, the subject matter of Example 26 includes, wherein to output the indication, the processor is further to output information indicating coverage of the femoral head component over the acetabular component and the force imparted on the femoral head component by the trunnion.

In Example 28, the subject matter of Examples 26-27 includes, wherein the trunnion is an adjustable trunnion configured to include a changeable shaft length between a head portion configured to receive the femoral head component and a base portion.

In Example 29, the subject matter of Example 28 includes, wherein the changeable shaft length is controlled by a height controller to extend the head portion away from the base portion.

In Example 30, the subject matter of Examples 21-29 includes, wherein to output the relative orientation includes to output the relative orientation to a heads-up display, an augmented reality display, or a display screen.

In Example 31, the subject matter of Examples 21-30 includes, wherein the relative orientation includes a patient-specific assessment of alignment of the acetabular component.

In Example 32, the subject matter of Examples 21-31 includes, wherein the femoral component is a trial component and the acetabular component is a standard implant selected from a standard set of implants provided by an implant manufacturer.

In Example 33, the subject matter of Examples 21-32 includes, wherein the femoral head component further includes the processor and wireless communication circuitry.

In Example 34, the subject matter of Examples 21-33 includes, wherein the femoral head component further includes a battery to power the processor.

Example 35 is a method for assessing orientation and dynamics of a hip arthroplasty component, the method comprising: using processing circuitry to: obtain initial magnetic field information using a magnetometer within a femoral head component; register an initial position based on the initial magnetic field information using a hall effect sensor within the femoral head component; obtain updated magnetic field information using the magnetometer; determine a change in orientation from the initial position of the femoral head component relative to an acetabular component based on a change between the initial and the updated magnetic field information; and output an indication based on the relative orientation.

In Example 36, the subject matter of Example 35 includes, wherein using the processing circuitry further includes determining, based at least in part on the relative orientation, a risk-level for postoperative impingement, and wherein the indication includes the risk-level for postoperative impingement.

In Example 37, the subject matter of Examples 35-36 includes, wherein using the processing circuitry further includes determining, based at least in part on the relative orientation, a patient-specific assessment of alignment of the acetabular component, and wherein the indication includes output of the patient-specific assessment of alignment of the acetabular component.

Example 38 is a system for assessing orientation and dynamics of a hip arthroplasty component, the system comprising: a femoral head component including: a magnetometer to: obtain initial magnetic field information; and obtain updated magnetic field information when the femoral head component is moved during a range of motion test; and a hall effect sensor to: register an initial orientation based on the initial magnetic field information; and an output device to: output an indication based on a change in relative orientation from the initial orientation of the femoral head component in reference to an acetabular component, the change in relative orientation corresponding to a change from the initial magnetic field information to the updated magnetic field information.

In Example 39, the subject matter of Example 38 includes, wherein the output device is one of a display device including a user interface, a haptic feedback device, or a speaker to play an audible alert.

In Example 40, the subject matter of Examples 38-39 includes, wherein to output the indication, the output device is to output a visual indication of impingement or lack of impingement based on the magnetic field and preoperatively determined limits on one or more of an impingement criteria, a joint force criteria, or an orientation angle.

Example 41 is at least one machine-readable medium including instructions that, when executed by processing circuitry, cause the processing circuitry to perform operations to implement of any of Examples 1-40.

Example 42 is an apparatus comprising means to implement of any of Examples 1-40.

Example 43 is a system to implement of any of Examples 1-40.

Example 44 is a method to implement of any of Examples 1-40.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), memory cards or sticks, random access memories (RAMs), read only memories (ROMs), and the like.

What is claimed is:
1. A system for assessing orientation and dynamics of a hip arthroplasty component, the system comprising:
   an acetabular component including a magnetic component to emit a magnetic field;
   a femoral component including:

a femoral head configured to be accommodated by the acetabular component; and a sensor to detect the magnetic field; and processing circuitry to:

receive information from the sensor about the magnetic field;

determine coverage of the femoral component by the acetabular component based at least in part on the information received from the sensor;

output an indication based on the coverage; and receive predefined criteria including impingement criteria, joint force criteria, or an orientation angle prior to receiving the information, wherein the joint force criteria, the orientation angle, or the impingement criteria includes preoperative set points, and wherein the indication includes a visual indication of impingement or lack of impingement based on a comparison between the preoperative set points and the orientation angle.

2. The system of claim 1, wherein the sensor is a Hall effect sensor and the information from the sensor includes a measured voltage based on proximity of the sensor to the magnetic field.

3. The system of claim 2, wherein the measured voltage is directly proportional to a strength of the magnetic field.

4. The system of claim 1, wherein the predefined criteria includes a lower or upper magnitude limit for each of the predefined criteria.

5. The system of claim 1, wherein the indication includes a force imparted by the femoral component on the acetabular component.

6. The system of claim 1, wherein the sensor includes at least one of a Hall effect sensor, a reed switch, a proximity sensor, or a magnetometer.

7. The system of claim 1, wherein the sensor includes a plurality of sensors arranged in two intersecting arcs within the femoral head.

8. The system of claim 1, wherein the magnetic component is removable from the acetabular component.

9. The system of claim 1, wherein the magnetic component is a magnetic ring.

10. The system of claim 1, wherein to output the indication, the processing circuitry is to output the indication using a heads-up display, an augmented reality display, or a display screen.

11. The system of claim 1, wherein the indication includes a risk-level for postoperative impingement or an alert of an impingement.

12. The system of claim 1, wherein the indication includes a patient-specific assessment of alignment of the acetabular component including the relative orientation.

13. The system of claim 1, wherein the sensor comprises a sensor array including two orthogonal intersecting arcs of sensors.

14. The system of claim 1, wherein the processing circuitry is further configured to produce a coverage map using the coverage of the femoral component by the acetabular component.

15. A system for assessing orientation and dynamics of a hip arthroplasty component, the system comprising:

an acetabular component including a magnetic component to emit a magnetic field;

a femoral component including:

a femoral head configured to be accommodated by the acetabular component; and a sensor array including two orthogonal intersecting arcs of sensors, the sensor array to detect the magnetic field; and processing circuitry to:

receive information from the sensor about the magnetic field;

determine coverage of the femoral component by the acetabular component based at least in part on the information received from the sensor; and output an indication based on the coverage.

16. A system for assessing orientation and dynamics of a hip arthroplasty component, the system comprising:

an acetabular component including a magnetic component to emit a magnetic field;

a femoral component including:

a femoral head configured to be accommodated by the acetabular component; and a sensor to detect the magnetic field; and processing circuitry to:

receive information from the sensor about the magnetic field;

determine coverage of the femoral component by the acetabular component based at least in part on the information received from the sensor;

output an indication based on the coverage; and produce a coverage map using the coverage of the femoral component by acetabular component.

* * * * *

UNITED STATES PATENT AND TRADEMARK OFFICE
CERTIFICATE OF CORRECTION

PATENT NO. : 10,842,636 B2
APPLICATION NO. : 15/800915
DATED : November 24, 2020
INVENTOR(S) : Johannaber et al.

Page 1 of 1

It is certified that error appears in the above-identified patent and that said Letters Patent is hereby corrected as shown below:

In the Claims

In Column 20, Line 45, in Claim 16, after "by", insert --the--

Signed and Sealed this
Ninth Day of February, 2021

Drew Hirshfeld
*Performing the Functions and Duties of the*
*Under Secretary of Commerce for Intellectual Property and*
*Director of the United States Patent and Trademark Office*